United States Patent
Palsson et al.

(10) Patent No.: US 9,080,199 B2
(45) Date of Patent: Jul. 14, 2015

(54) METHOD TO GENERATE NOVEL BIOACTIVE MOLECULES

(75) Inventors: Bernhard Palsson, San Diego, CA (US); Pep Charusanti, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 6 days.

(21) Appl. No.: 13/825,792

(22) PCT Filed: Oct. 28, 2011

(86) PCT No.: PCT/US2011/058450
§ 371 (c)(1),
(2), (4) Date: May 1, 2013

(87) PCT Pub. No.: WO2012/058630
PCT Pub. Date: May 3, 2012

(65) Prior Publication Data
US 2013/0211100 A1    Aug. 15, 2013

Related U.S. Application Data

(60) Provisional application No. 61/408,417, filed on Oct. 29, 2010.

(51) Int. Cl.
| | |
|---|---|
| C12P 39/00 | (2006.01) |
| C12Q 1/18 | (2006.01) |
| C12N 1/20 | (2006.01) |
| C12R 1/465 | (2006.01) |
| C12P 1/06 | (2006.01) |

(52) U.S. Cl.
CPC .. C12Q 1/18 (2013.01); C12N 1/20 (2013.01); C12P 1/06 (2013.01); C12P 39/00 (2013.01); C12R 1/465 (2013.01)

(58) Field of Classification Search
CPC .......................................... C12P 39/00
USPC .............................................. 435/42
See application file for complete search history.

(56) References Cited

U.S. PATENT DOCUMENTS

| | | | |
|---|---|---|---|
| 8,314,071 | B2 | 11/2012 | Sinskey et al. |
| 2010/0215620 | A1 | 8/2010 | Yang et al. |
| 2010/0249051 | A1 | 9/2010 | Sinskey et al. |

FOREIGN PATENT DOCUMENTS

| | | |
|---|---|---|
| EP | 2210935 A1 | 7/2010 |
| WO | WO 2008/073900 A1 | 6/2008 |

OTHER PUBLICATIONS de la Fuente et al., "Mutants of *Streptomyces clavuligerus* with Disruptions in Different Genes for Clavulanic Acid Biosynthesis Produce Large Amounts of Holomycin: Possible Cross-Regulation of Two Unrelated Secondary Metabolic Pathways," *J. Bacteriology* (2002), 184(23):6559-6565, American Society for Microbiology.

*Primary Examiner* — Robert Havlin
(74) *Attorney, Agent, or Firm* — DLA Piper LLP (US)

(57) ABSTRACT

The present invention describes a method to generate new chemical entities (NCEs) that have well-defined activities such as, but not limited to, anti-bacterial, antifungal and anthelmintic effects. The NCEs are generated through adaptive evolution of one microbe (the producer) against another organism or cell type (the target). The producer is made to compete against the target over time by co-culturing the two together and serially passing the producer organism until the producer adaptively evolves by synthesizing an NCE(s) that inhibits growth of or kills the target. The molecular structure of the chemical entity (or entities) is then elucidated using tools from genomics, molecular biology, computational biology, analytical chemistry, organic chemistry and related fields.

7 Claims, 19 Drawing Sheets

METHOD TO GENERATE NOVEL BIOACTIVE MOLECULES

CROSS-REFERENCE TO RELATED APPLICATIONS

This application is a 35 USC §371 National Stage application of International Application No. PCT/US2011/058450 filed Oct. 28, 2011, now pending; which claims the benefit under 35 USC §119(e) to U.S. Application Ser. No. 61/408,417 filed Oct. 29, 2010, now expired. The disclosure of each of the prior applications is considered part of and is incorporated by reference in the disclosure of this application.

GRANT INFORMATION

This invention was made with government support under Grant Nos. GM062791 and GM071808 awarded by the National Institutes of Health. The government has certain rights in the invention.

BACKGROUND OF THE INVENTION

1. Field of the Invention

This invention relates generally to methods of identifying bioactive small molecules from bacteria, fungi, and other microbes and more specifically to bioactive antibiotics, antifungals, and anthelmintics.

2. Background Information

Bacteria belonging to the order Actinomycetales, in particular those of the genus *Streptomyces*, constitute the most important and prolific source of antibiotics for medical, veterinary, and agricultural use. *Streptomyces* spp. are filamentous, non-motile bacteria found predominantly in soil and marine sediment. Unlike most other bacteria, they have complex secondary metabolic pathways that enable them to synthesize numerous structurally diverse molecules with a broad spectrum of bioactivity, especially antibiotics. Beginning with streptothricin and streptomycin in the early 1940s, the order Actinomycetales has yielded approximately 3000 known antibiotics. About 90% of these compounds were originally isolated from a *Streptomyces* spp. bacterium or are semi-synthetic derivatives of naturally-occurring molecules produced by a member of the *Streptomyces* (PMID: 11702082). Several notable examples include tetracycline (*Streptomyces aureofaciens*), chloramphenicol (*Streptomyces venezuelae*), vancomycin (*Amycolatopsis orientalis*), daptomycin (*Streptomyces roseosporus*), fosfomycin (*Streptomyces fradiae*), streptomycin (*Streptomyces griseus*) and erythromycin (*Saccharopolyspora erythraea*). A more extensive but not exhaustive list of antibiotics and the bacterium from which they were first isolated has been compiled in Practical *Streptomyces* Genetics (ISBN: 0708406238).

Although most famous for antibiotic production, Actinomycetes also produce compounds that have other useful properties in human and veterinary medicine as well as agriculture. Many anti-cancer agents, antifungals, anthelmintics, immunosuppressants, and other drugs currently in clinical use are derivatives of compounds that were originally isolated from an Actinomycete. This list includes bleomycin (*Streptomyces verticillus*; anti-cancer); nystatin (*Streptomyces noursei*; antifungal); amphotericin B (*Streptomyces nodosus*; antifungal); avermectin (*Streptomyces avermitilis*; anthelmintic); and rapamycin (*Streptomyces hygroscopicus*; immunosuppressant). Among a myriad of uses in agriculture, compounds isolated from Actinomycetes have been used as insecticides, herbicides, and to prolong the shelf-life of packaged foods. Specific examples from these areas are spinosyns (*Saccharopolyspora* spp.; insecticides) and natamycin (*Streptomyces natalensis*; food preservative).

Many bioactive compounds produced by *Streptomyces* spp., including antibiotics, fall into three main chemical classes: polyketides, non-ribosomal peptides, or hybrids of the two. As the name suggests, polyketides contain multiple ketone groups that are sometimes reduced to a lower oxidation state during various biosynthesis steps. This class of molecules is synthesized by polyketide synthases (PKS), a family of enzymes whose protein structure and corresponding genes are frequently organized in a modular structure. In turn, each module within the protein frequently contains several catalytic domains that have very specific functions. Three domains, thiolation, condensation, and adenylation, make up the core of each module. The coordinated action of each domain within each module leads to step-wise biosynthesis of polyketides that has been likened to an assembly line process. Tailoring enzymes then modify the polyketide, for example through glycosylation, oxidation, alkylation, and other chemical modifications, to generate the final structure. Non-ribosomal peptides are characterized by the presence of multiple contiguous amino acid residues within the molecule, for example β-lactams, vancomycin, and daptomycin, and are synthesized without the need for an mRNA template or the ribosome. As with PKS enzymes, non-ribosomal peptide synthases (NRPS) also have a modular organization, and many non-ribosomal peptides frequently undergo post-NRPS chemical modifications. The number of modules in PKS, NRPS and hybrid PKS/NRPS systems can vary over a wide range. *Streptomyces albulus* contains an NPRS cluster made up of only one module (PMID: 18997795), but more commonly there are several. These observations make clear that, fundamentally, the genome sequence of a producer organism defines the chemical structure of all polyketides, non-ribosomal peptides, and hybrid polyketide-non-ribosomal peptides it synthesizes.

The proven ability of Actinomycetes to produce clinically useful antibiotics, the deep knowledge acquired regarding their biology, and the existence of genetic manipulation tools for several species within this family of bacteria continue to make Actinomycetes an attractive source for new antibiotics. Indeed, *Streptomyces coelicolor* A3(2) (PMID: 12000953) and *Streptomyces avermitilis* (PMID: 12692562) were the first two members of this genus to be fully sequenced and found to have the capacity to produce many more secondary metabolites than had been isolated from either organism at the time. This pattern continues to hold even as the genomes from increasing numbers of Actinomycetes are fully sequenced (PMID: 17369815, 20624727, 18375553). Known, cultivable Actinomycetes consequently appear to harbor a large reservoir of potentially commercially-valuable bioactive compounds that still await discovery. In addition, it has been estimated that less than 1 part in $10^{12}$ of the earth's soil surface has been screened for Actinomycetes (Baltz, R. H. Antibiotic discovery from actinomycetes: will a renaissance follow the decline and fall? *SIM News* 55, 186-196 (2005)), a number that suggests the biosphere contains an even greater amount of undiscovered useful compounds.

These observations have spurred intense efforts to discover new bioactive molecules from Actinomycetes using a variety of methods. One common tactic is to search different parts of the world for new bacteria capable of producing secondary metabolites. Recent efforts focused on the marine environment in particular have led to the discovery of scores of new Actinomycetes (PMID: 12548698, 19406773, 19625431, 19196758, 19329599, 16538400). One of them, *Salinospora*

*tropica*, was found to produce a compound, salinosporamide A, that exhibited potent and selective cytotoxicity against cancer cells. It has now advanced to clinical trials in humans for the treatment of multiple myeloma. Notwithstanding successes such as this one, high false positive rates plague bioprospecting because the most abundant antibiotics in nature appear to be those that have already been discovered, a circumstance that interferes significantly with the screening process. For example, about 1% of soil actinomycetes produce streptomycin, first discovered in the 1940s, whereas daptomycin was discovered in the 1980s after screening an estimated $10^7$ actinomycetes (PMID: 18524678).

Another common tactic is to grow organisms under different culture conditions and then test the growth media for bioactivity. Variables such as temperature, pH, composition of the growth medium, and the concentration of each component all influence secondary metabolite production in Actinomycetes. The presence or absence of another organism(s) in the same growth environment is yet another variable. Co-cultures involving two or more organisms might stimulate one of them to produce a compound not normally synthesized when they are grown as monocultures through secretion of key, uncharacterized signaling molecules or as a defensive mechanism. On the other hand, this approach suffers from several disadvantages that make successful implementation challenging. For example, it is nearly impossible to determine a priori the optimal growth environments that best stimulate production of different secondary metabolites, necessitating a large amount of trial and error. High-throughput miniaturized fermentation and screening methods mitigate but do not solve this problem since the number of different growth media is almost limitless. The use of co-cultures faces the same difficulty: the identity of appropriate helper strains, defined as organisms that stimulate others to produce bioactive molecules in co-culture, is not readily known.

A third method is to introduce random mutations into the genome of producer organisms. Random mutagenesis is a broad, well-established approach to microbial strain improvement; however, it also relies on the occurrence of a low probability event, the acquisition of one or more beneficial mutations, to succeed. Furthermore, while most random mutagenesis techniques such as UV irradiation, chemical mutagenesis, and error-prone PCR efficiently generate point mutations or small indels, they induce larger mutations such as large duplications, deletions, transpositions, or other genome rearrangements much less effectively. Conversely, mutational methods that focus on large genome rearrangements, such as whole genome shuffling, do not generate small point mutations efficiently. In this way, current random mutagenesis techniques only sample a small subset of all possible mutations even if multiple methods are utilized. An additional drawback is that strains usually become less fit as they acquire more mutations, a side-effect that can nullify their utility even though they might develop one or more beneficial mutations that confers a desired phenotype.

Targeted mutagenesis of key genes or pathways is a fourth method. This strategy is especially appealing for novel antibiotic production in Actinomycetes because the gene targets are well-defined: the PKS and NRPS clusters. Since these clusters contain distinct modules, their structural organization opens the possibility that different modules can be swapped among different clusters and among different *Streptomyces* spp., thereby potentially leading to numerous new molecules. The viability of this approach, referred to as combinatorial biosynthesis, has been demonstrated by the synthesis of 154 different hybrid PKS systems using individual modules from seven different PKS clusters in various streptomycetes and myxobacteria (PMID: 16116420 and 16187094). Each of the 154 hybrids contained two modules. The combinatorial biosynthesis of lipopeptide antibiotics related to daptomycin (PMID: 17090667) and spinosyn analogs (PMID: 17190446) are two other examples. Despite these successes, combinatorial biosynthesis has not led to an abundance of new bioactive molecules from Actinomycetes due to several technical challenges. For instance, the linker regions that connect one module to the next can vary within a given cluster and from one cluster to another, making it difficult to establish in a systematic way where one module ends and the next one begins. Moreover, swapping large pieces of protein-coding DNA inevitably impacts proper protein folding, frequently resulting in mis-folded proteins that are non-functional. More broadly, evidence is accumulating that mutations in other genes besides PKS and NRPS clusters also serve to improve existing antibiotic production or activate new ones (PMID: 20524642 and 19396160). Thus, a narrow focus on mutating only PKS and NRPS clusters could miss other important mutation sites in the genome.

The cloning and heterologous expression of antibiotic biosynthesis gene clusters in alternative host organisms is yet another method. This strategy is particularly attractive when no genetic manipulation system exists for the native producer, the sequence of interest comes from a metagenomic library, or a microorganism that cannot be cultured. These advantages are balanced by several disadvantages that limit the use of this tool for widespread antibiotic discovery. First, heterologous gene expression can lead to metabolic imbalances in the new host that then negatively impact the growth rate of the host or production of the new molecule. Second, cloning large stretches of DNA in streptomycetes is time consuming as the procedure still relies on classical methods using cosmids, fosmids, and similar constructs. Third, unknown but necessary cofactors, substrates or proteins might not be present in the new host.

The wealth of new antibiotics that undoubtedly remain to be discovered and the proven capability of existing techniques, such as those outlined above, to uncover new compounds argue for their continued implementation in the search for new antibiotics. At the same time, all existing techniques have drawbacks such that none constitute a single solution to the myriad of challenges faced during antibiotic discovery. As a result, there continues to be a need to develop new technologies and methods that complement and improve various aspects of the discovery process. This invention discloses a new method that allows for the discovery of novel, targeted antibiotics and, more generally, other types of bioactive compounds from a producing organism.

SUMMARY OF THE INVENTION

The present invention is based on the seminal discovery that new chemical entities (NCEs) are generated through adaptive evolution of one microbe (the producer) against another organism or cell type (the target). The producer is made to compete against the target over time by co-culturing the two together and serially passing the producer organism until the producer adaptively evolves by synthesizing one or more NCEs that inhibits growth of or kills the target. The molecular structure of the chemical entity (or entities) is then elucidated using tools from genomics, molecular biology, computational biology, analytical chemistry, organic chemistry, and related fields. The present invention describes a method to generate new chemical entities (NCEs) that have well-defined activities such as, but not limited to, anti-bacterial, antifungal, and anthelmintic effects.

In one embodiment, the present invention relates to a method for identifying a bioactive compound in a culture. The method includes (i) co-culturing two or more organisms, at least one organism is a producer and at least one other organism is a target; (ii) detecting inhibition of growth of the target organism(s); and (iii) detecting the presence of one or more bioactive compounds in the co-culture, thereby identifying a bioactive compound. In one aspect, the method further includes isolating from the co-culture one or more producers after detecting inhibition of growth of the target organism(s). In another aspect, the method includes isolating from a producer at least one compound with bioactivity against the target(s) from the co-culture of the competing organisms. The method also includes repeating (i)-(iii) at least once with the isolated producer and the target where the target may be obtained from any source.

In one aspect, the method further includes identifying the bioactive compounds by chemical structure elucidation means including, but not limited to, mass spectrometry (MS) and nuclear magnetic resonance spectroscopy (NMR).

In another embodiment, the co-culture includes *Streptomyces clavuligerus* or *Staphylococcus aureus*. The producer can be a *Streptomyces clavuligerus* strain. In a particular aspect, the target is drug-resistant *Staphylococcus aureus*. In other aspects, inhibition of growth of the target organism is the appearance in the co-culture of a zone of inhibition (ZOI).

In one embodiment, the present invention relates to isolated *Streptomyces clavuligerus* strains, including clavu7 and NL2-c4, according to the method of the invention. In another aspect, the present invention relates to one or more isolated bioactive compounds according to the method of the invention.

Provided herein is a method of identifying genomic mutations in an organism. The method includes (i) co-culturing two or more organisms, wherein at least one organism is a producer and at least one other organism is a target; and (ii) detecting one or more mutations in the nucleic acid sequence of the producer genome as compared to a wild-type (WT) producer genome prior to co-culture, thereby identifying genomic mutations in the producer organism. The method also includes introducing the genomic mutation(s) into a strain of the producer prior to co-culture. In one aspect, the mutation(s) is identified by independent partial- or whole-genome re-sequencing of the producer.

DETAILED DESCRIPTION OF THE INVENTION

Figure 1:
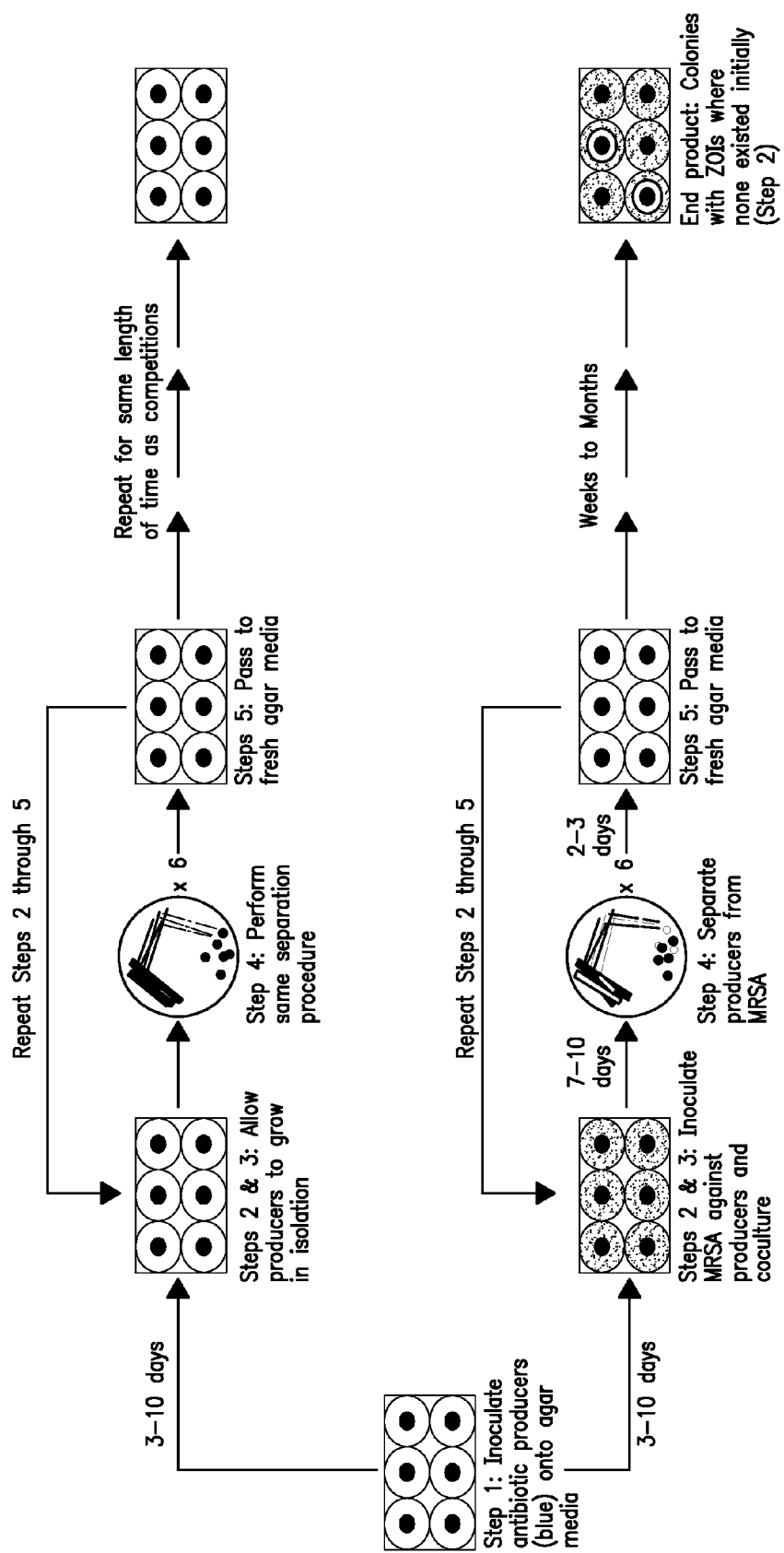
FIG. 1 is a schematic representation of an experimental protocol for the method of the invention. Black spots indicate producers of bioactive compounds such as bacteria from the genus *Streptomyces*. Gray areas indicate the target organism (for example, drug resistant *Staphylococcus aureus*). Two of six colonies are depicted here as adaptively evolving to produce a new bioactive compound against drug-resistant *Staphylococcus aureus*, but the actual number will vary with each experiment.

This invention describes a method to generate novel bioactive compounds with well-defined function, in particular but not limited to antibacterials, antivirals, antifungals, and anthelmintics. The central idea underlying the method is that organisms that must compete for space, nutrients, and other essential factors necessary for growth and survival will adaptively evolve over time to produce compounds that kill or inhibit growth of any competitors and/or predators, compounds that might then be exploited for human use.

The method described herein includes repeatedly competing a producer organism against a target organism and separating the two organisms in order to obtain pure isolates of the producer. Once separated, the producer is then re-competed against the target to begin the cycle anew, thereby introducing the element of time and adaptive evolution into the experiment. The adaptive evolution phase ends when the producer adaptively evolves and synthesizes a compound that shows bioactivity against the target organism, for example by inhibiting the growth of or killing the target organism. The co-cultures can be carried out either in liquid media, on a solid support such as agar plates, or some combination of the two (e.g., competition in liquid media in one round and competition on a solid support in another round).

"Microbe" or "microorganism": Used interchangeably, a microbe or microorganism is any free-living member from the three kingdoms of life (eukaryotes, prokaryotes and Archaea) that is too small to be seen with the naked eye. While aggregates of microorganisms can frequently be seen with the naked eye, individual cells of microorganisms, each of which is free-living and can survive and reproduce on their own, cannot. Several common examples include bacteria, fungi, protists, Archaea, microscopic plants (e.g., algae) or microscopic animals (e.g., nematodes). We include viruses in our definition of these two words as well despite debate regarding their status as free-living or not.

Organism: An organism includes "microbes" as defined above as well as all free-living Archaea and eukaryotes large enough to be seen with the naked eye.

Producer and non-producer: A "producer" is any microorganism that synthesizes and secretes a compound that kills or inhibits growth of another microorganism(s). The present invention describes a method to create producers from microorganisms that do not initially synthesize and secrete bioactive compounds against a competitor. A "non-producer" is any microbe that does not synthesize a bioactive compound (s) against the competitor.

"Competitor," "target," or "target organism": Used interchangeably, a competitor, target, or target organism is any organism whose growth one wishes to inhibit, for example by outright killing, by preventing it from growing further, or by preventing the target from reproducing. The competitor or target organism need not be free-living; it may be a cell line.

Cell line: A cell line is a non-free living population of cells that will proliferate indefinitely given appropriate fresh culture medium. Once the medium has been removed however, a cell line can no longer survive because it is not capable of acquiring nutrients on its own. This term usually refers to cell populations derived from multi-cellular eukaryotes, especially from plants or animals.

Small molecule: A small molecule is a type of compound (as defined above) that has a molecular weight of less than 1000 Daltons. Small molecules do not include biopolymers such as DNA, RNA, proteins, and polysaccharides; however, small molecules can include their constituent monomers.

Compound: A compound is any molecule composed of any of the chemical elements (hydrogen, carbon, nitrogen, etc.).

Metabolites: A metabolite has two definitions. It can be any chemical produced by an organism as an intermediate or end-product of its metabolism, or it can be what remains after a small molecule given exogenously, such as a drug, has been broken down inside a host.

"Adaptive evolution" or "adaptation": As used herein, "adaptive evolution" and "adaptation" are both used interchangeably and refer to the process whereby, over time, a microorganism that is initially not a producer becomes a producer. The producer phenotype arises because, over time, genetic and/or transcriptional changes occur in a non-producer that eventually confers the microbe the ability to synthesize a bioactive compound(s). This ability, in turn, arises from long-term co-culture and competition between a producer and a competitor and serial passage of the producer.

Serial passage: Serial passage and its verb "to serially pass" is the process whereby a portion of a population of microorganisms is repeatedly transferred to a new growth environment that is identical or nearly identical to the one in which the microorganism has just experienced. The transfer can occur in one or more steps, and there can be more than one passage. An example of a one-step serial passage of microbes growing in liquid media comprises: 1) measuring the concentration of the culture by optical density or other means; and 2) transferring a portion of the culture to a new flask containing new growth media. Normally, the composition of the new growth medium is identical to the medium from which the microbes have just been taken but before any microbes had been introduced; however, in certain cases, the media or more generally the growth environment can vary by the addition, subtraction, or modification of certain components such as chemical mutagens.

"Culture medium," "culture media," "medium" or "media": Used interchangeably, these four terms refer to the chemical environment accessible to an organism. Media are typically composed of water with other additional nutrients. Media are frequently in liquid form, but the media can be solidified by adding a solidifying agent such as agar or agarose. The ingredients may be purified chemicals (i.e., "defined" media) or complex, uncharacterized mixtures of chemicals such as extracts made from milk or blood. Standardized media are widely used in laboratories. Examples of media for the growth of microorganisms include, but are not limited to, Luria-Bertrani broth and M9 minimal medium.

The term "minimal" when used in reference to media refers to media that support the growth of an organism, but are composed of the minimal set of compounds that will support growth of an organism. For example, M9 minimal medium is composed of the following ingredients dissolved in water and sterilized: 48 mM $Na_2HPO_4$, 22 mM $KH_2PO_4$, 9 mM NaCl, 19 mM $NH_4Cl$, 2 mM $MgSO_4$, 0.1 mM $CaCl_2$, 0.2% carbon and energy source (e.g., glucose).

Growth environment: A growth environment is the combination of all factors that permit an organism to grow. These include, but are not limited to, temperature, humidity, the culture medium, presence or absence of oxygen, presence or absence of light, pH, and the size and shape of the flask in which the organisms are growing.

Nutrient: A nutrient is any chemical compound that supports growth of an organism, for example water, vitamins, sugar, carbohydrates, and fatty acids.

Co-culture: A co-culture is growth of two or more organisms in the same growth environment, for example in liquid broths or agar plates, such that they are in physical contact with each other or interact chemically through exchange of secreted metabolites.

"Bioactive" and "bioactive compound": Used interchangeably, a "bioactive compound" or a compound described as "bioactive" is any molecule that 1) kills or inhibits growth of a target organism, as defined above; 2) inhibits biofilm formation of microorganisms; 3) disrupts existing biofilms of microorganisms, for example by causing the individual cells in the biofilm to break apart from each other and disperse; or 4) prevents an organism from reproducing, for example by disrupting seed formation in plants or by sperm/egg formation in animals such as insects. Examples of bioactive compounds include, but are not limited to, small molecules (as defined above), nucleic acids, proteins, antibodies, peptide nucleic acids, and others. It is possible for bioactive compounds to have molecular weights greater than 1000 Daltons that are neither polymers nor proteins. One example is the antibiotic daptomycin (Cubicin) which has a molecular weight of 1619.6 grams per mole.

"Antibiotic" and "antimicrobial compound": Used interchangeably, an "antibiotic" or "antimicrobial compound" is any molecule that kills or inhibits growth or a microorganism. In this way, an "antibiotic" or "antimicrobial compound" is a specific type of bioactive compound (as defined above) that affects only microorganisms.

"Microbial colony" or simply "colony": On an agar plate, a colony is a collection of microbial cells that is completely surrounded by agar such that the colony does not physically contact other microbes on the agar plate. A colony need not be comprised of one single microbial species; a colony can contain multiple different microbes from all three kingdoms (prokaryotes, eukaryotes, Archaea), in which case the colony is referred to as "mixed."

Zone of inhibition: Abbreviated ZOI and seen on agar plates only, a zone of inhibition is an area immediately surrounding a microbial colony or a paper disk instilled with one or more chemical compounds in which no other organism has grown. When surrounding a microbial colony, the presence of a ZOI indicates that the colony is secreting one or more chemical compounds into the agar that inhibits growth or kills other organisms within the ZOI. When surrounding a paper disk instilled with one or more chemical compounds, the presence of a ZOI indicates that the compound(s) has diffused into the agar away from the disk and inhibited growth or killed other organisms within the ZOI. The size of a ZOI is directly proportional to how sensitive an organism is to the compounds secreted by the microbial colony or diffusing away from the disk.

Antibiotic biosynthesis gene cluster: A set of genes, usually contiguous, all of which are necessary to synthesize a bioactive compound.

Cryptic gene: A gene hypothesized to encode corresponding mRNA and protein but one for which neither the mRNA nor the protein has been detected yet.

New chemical entity: Abbreviated NCE, a "new chemical entity" is a molecule whose structure has not been previously described. An NCE cannot be found in any database of chemical compounds such as SciFinder Scholar, AntiBase, Crossfire Beilstein, and others.

Genome: A genome refers to the entire chromosome and all extra-chromosomal elements (e.g., plasmids) within a microbe.

Chromosome: An organized structure of DNA that contains most of a cell's genetic information. Chromosomes are often associated with proteins and/or RNA that help package the chromosomes into a smaller volume, regulate transcription, and serve other functions.

Extra-chromosomal elements: A DNA element within a cell but not within the chromosome. Some common examples include plasmids, cosmids, fosmids, and bacterial artificial chromosomes (BAC).

Gene: A gene is any stretch of DNA that is transcribed into RNA. The entire RNA may be translated into protein but does not necessarily have to do so. The entire RNA may be noncoding, or only portions of the RNA may encode protein due to the presence of untranslated regions such as introns and poly-adenylation tails. The term "gene" encompasses both genomic DNA and cDNA, and includes all regulatory elements at both the 5' and 3' termini such as promoters that control transcription of the gene into mRNA.

Base pair: A base pair refers to the pairing of two nucleotides via hydrogen bonding, for example adenine (A) with thymine (T) and cytosine (C) with guanine (G) in double-stranded DNA. Uracil (U) substitutes for thymine in RNA. The number of base pairs may be used as a measure of DNA length.

Mutation: A mutation refers to any change in the DNA sequence of an organism when compared to the DNA from another organism. Two examples of mutations are single nucleotide polymorphisms and indels.

Single nucleotide polymorphism: Abbreviated SNP (plural: SNPs), single nucleotide polymorphisms are one base pair differences in the DNA of two organisms of the same species. A SNP can also refer to one base pair differences in the DNA between two or more paired chromosomes in organisms with more than one chromosome.

Indel: Short for "insertion/deletion," an indel is a type of mutation defined by the insertion, deletion, or combination thereof of one base pair or multiple contiguous base pairs in an organism's DNA when compared to a reference genome.

Plasmid: A plasmid is a double-stranded DNA molecule that can exist and replicate independently of the chromosome or may be integrated into it.

Cosmid: A cosmid is a type of plasmid that contains lambda phage cos sites. Unlike plasmids, cosmids can be packaged in phage capsids.

Fosmid: Fosmids are similar to cosmids in that both are types of plasmids that contain cos sites, but the two differ in that fosmids are derived from the F-factor plasmid.

Bacterial artificial chromosome: Abbreviated BAC, bacterial artificial chromosomes are derived from $E.$ $coli$ F-factor plasmid but do not contain cos sites.

The choice of target organism determines what type of molecule is generated in the end. For example, if the target organism is a bacterium, then the end product after adaptive evolution will be antibacterial compounds; if the target organism is a fungus, the end product will be antifungals; if the target organism is a nematode, the end product will be anthelmintics; if the target organism is cancerous mammalian cells, the end product will be anti-cancer compounds; and so forth.

The method disclosed herein includes:

Selection of a microbe that has the capability to produce bioactive compounds. The microbe can be either a natural isolate or one that has been engineered to have this capability, for example by inserting genes for antibiotic biosynthesis on a plasmid or into the chromosome or by deleting regions of DNA within the chosen producer microbe.

Selection of a target whose growth one desires to inhibit. The target can be another whole organism such as another microbe, nematode, or insect, or it can be a cell line. The target can be either a natural isolate or one that has been engineered to have a desired property, for example by inserting genes for antibiotic resistance into the organism.

Co-culturing the producer against the chosen target. If carried out in liquid culture, the two organisms are introduced into the same flask containing a liquid growth medium that supports expansion of both. They are then allowed to grow over a period of time. Co-culturing the two organisms together in this manner is hypothesized to stimulate competition between them for space, nutrients and other resources, competition that drives the producer to synthesize one or more bioactive molecules that inhibits growth of the competitor. The time in which the two organisms are allowed to compete against one another can vary and does not have to remain the same from one passage to the next. The amounts of each organism introduced into the flask can vary as well. For example, both might be introduced into the flask such that they have the same initial concentrations; one might have a higher initial concentration than the other; or one might be allowed to grow for a period of time as a monoculture before the second is introduced into the flask.

Co-cultures done on solid support such as agar plates follow the same protocol as for liquid-based co-cultures. The two organisms are placed onto the same solid growth media and allowed to grow in each other's presence. The amount of time they spend together in co-culture and the amounts of each organism placed on the solid medium once again can vary and does not need to be the same from one passage to the next. In experiments involving streptomycetes, for example, one might place the streptomycetes on the solid medium several days or weeks before introducing the target organism since antibiotic production in streptomycetes normally occurs during stationary phase growth.

Separation of the two organisms to isolate the producer. After the two organisms are cultured together for a period of time, they are next separated in order to isolate the producer. This can be accomplished through any property that distinguishes the producer from the competitor, for instance size, charge, cell surface properties (e.g., the presence of a unique receptor on one organism but not the other), staining (e.g., Gram positive versus Gram negative), antibiotic susceptibility, auxotrophies, differential growth media (i.e., transferring the mixed population to a new growth medium that supports growth of only one of the organisms), streaking onto a solid growth medium (e.g., an agar plate) for single colonies, or other techniques. Separation can also involve, but does not require, use of a mechanical device such as fluorescence associated cell sorting (FACS) or microfluidics.

The cycle of co-culture and separation may be repeated one or more times. Once the two organisms have been separated, the producer is transferred to new growth media to begin a co-culture of the two once more. The competitor does not necessarily have to be transferred as well; however, it is necessary to serially pass the producer from one round to the next. The competitor can come from a source that has had no prior contact with the producer such as frozen stock cultures.

Each co-culture is assayed for detection of possible bioactive molecules. During and after each cycle, the growth medium is routinely assayed for the presence of possible new bioactive molecules. Example assays include visually inspecting the mixed or separated system for reduced or no growth of the target organism, noting the presence of zones of inhibition (ZOI) surrounding the producer organism when the producer and competitor are co-cultured on solid support; and chemical analysis of the co-culture supernatant, for instance using HPLC.

Once the assay(s) produces a positive result, the producer organism is characterized in more detail to definitively determine the identity of the bioactive molecule. This work typically involves standard techniques used in analytical and organic chemistry whereby the growth medium itself or extracts of the growth medium are fractionated on a chromatography or similar system and each fraction is tested for bioactivity. Fractions showing bioactivity are fractionated further (if necessary) and again tested for bioactivity. Once a pure, bioactive fraction has been obtained, it is then subjected to mass spectrometry (MS), nuclear magnetic resonance spectroscopy (NMR), UV-visible spectroscopy, IR spectroscopy and other analytical methods for elucidation of its chemical structure.

Many organisms produce compounds that are bioactive against other organisms. For example, soil bacteria of the genus *Streptomyces* produce compounds that inhibit growth of other bacteria, and these compounds have been exploited by man for use as antibiotic medicines.

The central idea underlying the method described herein is as follows: if a producer organism of interest such as a *Streptomyces* spp. bacterium produces bioactive compounds that do not inhibit the growth of the target organism(s) or produces relatively small amounts of bioactive compounds that inhibit the growth of target organisms, and the streptomycetes and the target organism must compete with each other (e.g., competition for nutrients), then the producer might evolve in such a way as to produce new compounds or up-regulate biosynthesis of existing compounds that do inhibit growth of the competitor. Thus, the method combines competition with adaptive evolution as a possible way to generate new compounds or obtain mutant strains that synthesize a known bioactive compound in greater quantities than what is obtained from the wild-type strain. In one embodiment, the method includes:

Selection of two or more organisms, one of which produces no bioactive compounds whatsoever or produces compounds that initially have no apparent effect on the other competing organism(s).

Co-culturing the organisms together, and use an appropriate bioassay to determine whether a compound with the desired bioactive property has been produced. If the bioassay reveals that a compound with the desired properties has not been obtained, then select and purify the organism of interest (i.e., the producer) from the co-culture mix.

Co-culturing the target together and the isolated producer i.e., serially pass the producer organism until the producer adaptively evolves and a positive bioassay has been obtained.

Isolating and characterizing the new bioactive compounds.

An example of the method of invention is illustrated in FIG. 1, where one bacterium (Strep) is competed against another (Staph) with the objective of finding a novel antibacterial compound. A positive bioassay in this case is the appearance of a halo or zone of inhibition around a Strep colony.

Examples of evolved strains generated by the competitive adaptive evolution method as described herein include clavu7 and NL2-c4, both generated from wild-type *Streptomyces clavuligerus* ATCC 27064. The clavu7 strain of *S. clavuligerus* can be stored long-term at −80° C. as mycelia in a liquid broth with approximately 20% glycerol.

Evolved strain clavu7 was found to produce greater amounts of holomycin, which inhibits growth of a drug-resistant strain of *Staphylococcus aureus* (strain N315), than the wild-type strain that was used to initiate the adaptive evolutions against N315. *Staphylococcus aureus* (strain N315) was isolated in 1982 and is known to be resistant to clindamycin, erythromycin, and many β-lactam antibiotics. Holomycin is a known antibacterial compound produced by certain defined mutants of *Streptomyces clavuligerus* (PMID 12426344). This compound has a molecular mass of 213.99 g/mole and a molecular formula of $C_7H_6N_2O_2S_2$.

Figure 9:
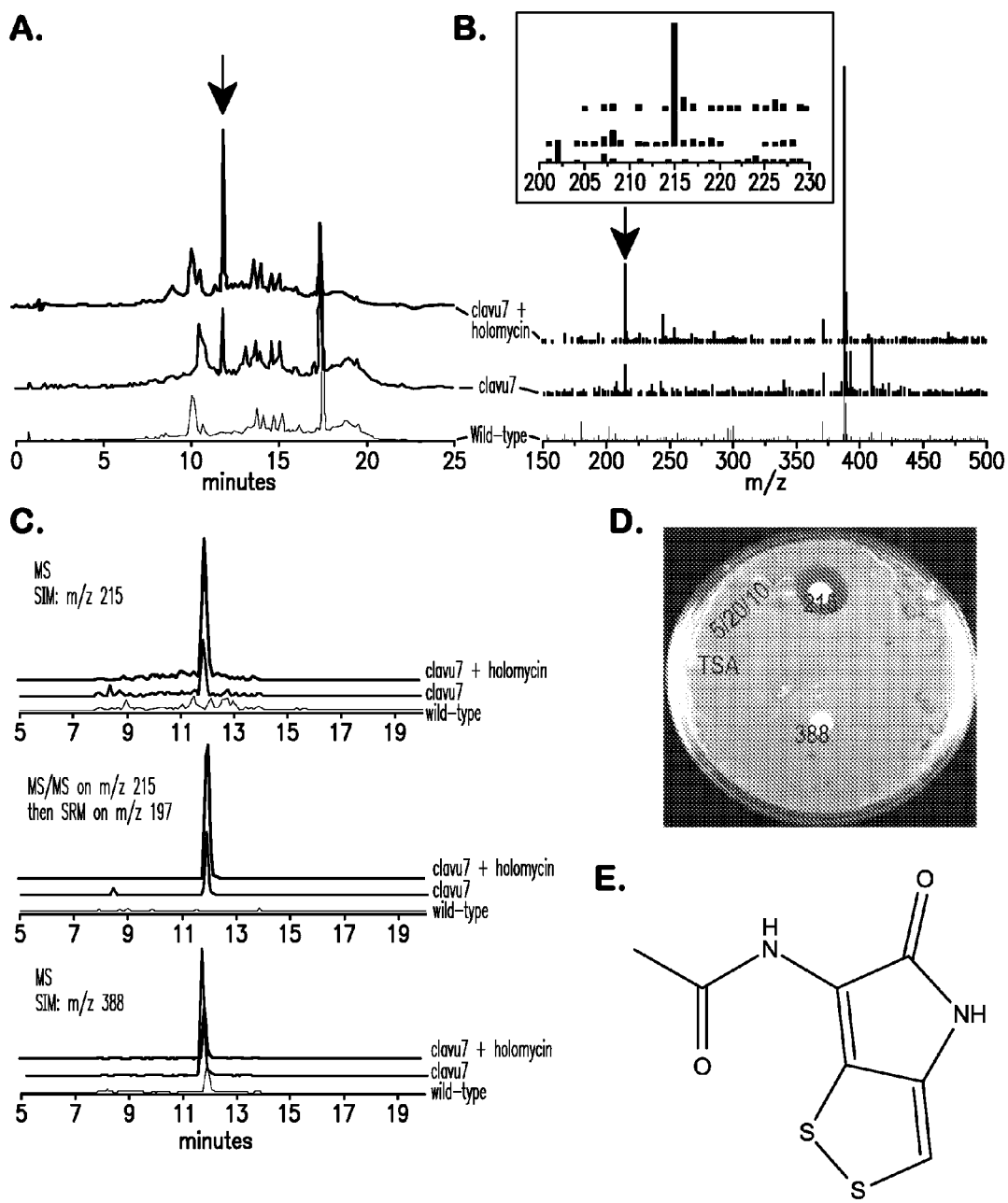
FIG. 9 is HPLC-MS data from extracts of wild-type *S. clavuligerus*, clavu7, and clavu7 spiked with holomycin. A. HPLC chromatograms of extracts from the three samples. The arrow indicates the peak corresponding to holomycin, which elutes at approximately 11.8 minutes. B-C. MS total ion monitoring at 11.8 minutes. There is an intense peak at m/z=388 that is present in both wild-type *S. clavuligerus* and clavu7 samples, but an ion with m/z=215 ([M+H]$^+$), which is holomycin and indicated by the arrow, can be detected in the clavu7 sample only. Inset. Magnification of the region surrounding m/z=215. D. is a photograph of cultures of MRSA N315 plated against a mutant strain of *S. clavuligerus* referred to as clavu7. E. depicts the chemical structure of the fragment that gives rise to the m/z=215 peak.

The identity of the bioactive compounds, such as holomycin (initially designated compound A) from clavu7, can be established through several means as described below. For example, when extracts of the agar immediately surrounding clavu7 colonies were separated via LC-MS and tested for bioactivity against *S. aureus* N315, the fraction eluting between 11 and 11.5 minutes showed bioactivity. There is a single peak in the chromatogram in this time window. A high resolution mass spectrum of this peak revealed the presence of a compound with a molecular formula of $C_7H_6N_2O_2S_2$, which is identical to that of holomycin. Moreover, when a sample of pure holomycin was added to the clavu7 extract and analyzed using the same LC-MS method, the only peak in the chromatogram that increased in size was the lone peak between 11 and 11.5 minutes. Both of these data confirm that the bioactive compound from clavu7 extracts is holomycin (FIG. 9).

Holomycin had a demonstrated mass-to-charge ratio (m/z) of 215 when analyzed by LC-MS, and co-eluted with another compound with m/z=388 when the mobile phase consisted of a linear gradient form 5% methanol in water to 50% methanol in water over 20 minutes. The two compounds were separated from one another by re-injecting the 11 to 11.5 minute fraction into the LC-MS system using an isocratic mobile phase of 30% methanol in water. Once separated, the two compounds were collected, concentrated by evaporating the solvent to a total volume of approximately 50 µL, and tested against S. aureus N315 to definitively determine which one is bioactive. This turned out to be m/z=215, which was identified as holomycin. Bioactivity testing is carried out by first spreading approximately 150 µL of an OD600~0.01 S. aureus N315 culture in TSB onto a TSA plate to create a lawn of S. aureus N315. Next, 25-30 µL of each sample is deposited onto 6 mm sterile filter disks. The disks are allowed to dry and then placed onto the S. aureus N315 lawn. This plate is incubated for 16-20 hours at 30° C., after which it was examined for the appearance of a zone of inhibition around the disks.

While holomycin was isolated from extracts of clavu7, which is a strain of S. clavuligerus that was evolved against drug-resistant S. aureus N315 using the method described herein, holomycin was neither detected from extracts of wild-type S. clavuligerus that was used to initiate the adaptive evolution process against S. aureus N315 nor evolved strain NL2-c4.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Generation and Identification of Clavu7 Strain and Holomycin

This example illustrates how the present method can be used to generate a mutant, adaptively-evolved strain that synthesizes larger quantities of an antibiotic than the wild-type strain. In this case, the producer organism was *Streptomyces clavuligerus* ATCC 27064 and the target organism was methicillin-resistant *Staphylococcus aureus* strain N315 (MRSA N315). MRSA N315 is resistant to erythromycin and many β-lactam antibiotics such as penicillin.

Wild-type S. clavuligerus mycelia or spores are first inoculated into a triple-baffled flask containing trypticase soy broth (TSB) and incubated at 28-30° C. A magnetic stir plate spun a stir bar inside the flask at approximately 1500-2000 rpm to aerate the liquid broth. Once the culture reached an optical density at 600 nanometers (OD600) between 0.08 and 0.13, 2 µL aliquots of the culture were spotted onto each of seven equidistant points on a trypticase soy agar (TSA) plate. If the culture was denser than 0.13, it was diluted with TSB until the measured OD600 value fell between 0.08 and 0.12. The use of an OD600 culture between 0.08 and 0.13, the use of a 2 µL dispensing volume, and the choice of seven spots per plate (versus a different number) were arbitrary; these values can vary from one experiment to another, depending on the growth characteristics of the producer. The plate containing the S. clavuligerus was placed in an incubator maintained at 28° C. for three days. On the third day, approximately 150 µL of an MRSA N315 OD600 culture between 0.008 and 0.013 (i.e., 10-fold lower concentration than the S. clavuligerus inoculum concentration) was spread onto the TSA plate containing the seven equidistant S. clavuligerus colonies such that MRSA N315 completely surrounded each of the seven colonies. Again, the incubation period and temperature for the producer organism and the inoculum concentration for the target organism can vary. The choice of three days and 28° C. for this particular experiment reflected recommended growth characteristics for S. clavuligerus. Approximately 16 to 24 hours after MRSA N315 was plated against S. clavuligerus, the plate was examined for the presence of a zone of inhibition (ZOI) surrounding the seven S. clavuligerus colonies. No conclusive ZOIs were seen.

After inspection, the plate was placed back in the incubator and remained there for another 4-6 days. The total co-culture time was consequently 5-7 days. Following this time, each of the seven S. clavuligerus colonies was streaked out onto fresh TSA plates that were then all incubated for 2-3 days at 28° C. For each of the seven replicates, an isolated S. clavuligerus colony appearing on their streak plates was next transferred to a single, fresh TSA plate that once again contained all seven replicates equally spaced apart. When no well-isolated colonies were available, portions of S. clavuligerus colonies or streaks that did not contact MRSA N315 were broken off and transferred instead. Streak plates on which only MRSA N315 grew were discarded and the corresponding S. clavuligerus colony re-streaked. The new TSA plate containing the seven S. clavuligerus replicates was again placed in a 28° C. incubator for three days. On the third day, MRSA N315 that had not previously contacted S. clavuligerus was spread onto the TSA plate as before to start a new round of co-culture. In this way, the seven S. clavuligerus replicates are serially passed from one round to the next but the MRSA N315 is not; the MRSA N315 used for each round of co-culture had not previously come into contact with S. clavuligerus.

These three steps, co-culturing S. clavuligerus with MRSA N315, inspecting the co-culture for evidence of a possible new bioactive molecule (i.e, ZOI), and separating the co-culture in order to isolate, purify, and serially pass S. clavuligerus, were repeatedly performed over a 4-5 month period. Several strains were isolated during this time that appeared to produce clear ZOIs against MRSA N315, each of which was grown up in liquid culture (TSB) and stored long-term at −80° C. as mycelia in 20% glycerol. A chemical analysis to determine the structure of the molecules responsible for the ZOI was then carried out. One isolate, designated "clavu7," was identified after three months.

The methods for chemical analysis are those routinely used in analytical and organic chemistry. In short, they entail 1) extracting the ZOI with a solvent or solvents that dissolve the bioactive molecules, which was 100% methanol in the case of clavu7; 2) concentrating the solvent, for example through use of a rotary evaporator, solid-phase extraction columns, and/or other means; 3) fractionating the sample, for example through use of one or more chromatography columns and/or one or more mobile phases per column; 4) collecting the fractions and testing them for bioactivity against the target organism, for example by evaporating the solvent to concentrate the fractions and performing a disk diffusion or broth dilution test; 5) purifying further the bioactive fraction (if necessary) in order to isolate each individual component, each of which is then tested again for bioactivity; 6) obtaining structural data for the bioactive molecules, for example through MS, NMR, IR, UV-vis and x-ray crystallography; and 7) analyzing and assembling the data to arrive at final structures for the bioactive molecules.

The specific extraction and structure elucidation procedure for the bioactive compound produced by clavu7 (holomycin) is as follows. First, a clavu7 culture was allowed to grow in TSB until it reached an OD600 between 0.08 and 0.13, after which 2 μL aliquots were spotted onto TSA plates (16-20 spots per plate). After four days incubation at 28° C., agar plugs extending approximately four millimeters from the edge of each clavu7 colony are excised from the rest off the agar plate, cut into small pieces, and soaked in 100% methanol for 20-30 minutes with constant stirring. To account for the possibility that MRSA N315 induced production and secretion of the clavu7 bioactive compounds, the same protocol used during the adaptive evolutions with plated MRSA N315 against clavu7 three days after plating clavu7 on the TSA plates was followed. However, subsequent LC-MS analysis comparing clavu7 extractions with and without MRSA N315 indicated that clavu7 produced the bioactive compounds even in the absence of MRSA N315. Therefore, plating MRSA N315 against clavu7 three days after clavu7 is spotted on the TSA plates when performing chemical analysis of the clavu7 bioactive compounds was discontinued. The methanol extract is decanted and either centrifuged or filtered through a membrane (or both) to remove the solid material. Next, the methanol is evaporated under vacuum until less than 5 mL remained, after which the concentrated solution was diluted 1:39 with water and passed through a Solid Phase Extraction (SPE) column. The specific SPE column and the protocol for its use to extract the bioactive compound are as follows: SPE column: Oasis MCX cation exchange SPE column (Waters Corp., Waltham, Mass.). The isolated bioactive compound was identified as holomycin as described below.

SPE Protocol:
i. Prep: 4 mL MeOH
ii. Prep: 4 mL deionized (DI) water
iii. Load sample. Maintain flow rate at 4-6 mL/min
iv. Wash: 3 mL 2% formic acid in water
v. Wash: 3 mL DI water
vi. Wash: 3 mL 20% methanol in DI water
vii. Elute and collect: 3 mL 70% methanol in DI water The 3 mL 70% methanol/water fraction was then concentrated under vacuum (e.g., using a centrifuge vacuum evaporator i.e., speed-vac or speed-yap) until it reached a volume of approximately 100 μL. Solid pellets that appeared during centrifugation were discarded. The bioactive compound was finally isolated from the ~100 μL semi-purified sample via two sequential HPLC separations. For both, the HPLC column was an Agilent C-18 column (Eclipse XDB-C18, 5 μm, 4.6 mm×150 mm) with flow rate of 1.0 mL/minute. About 0.20 mL/minute was delivered to an electrospray ionization (ESI) mass spectrometer and 0.80 mL/minute was delivered to waste.

The HPLC conditions for the first run were as follows. These conditions are also depicted diagrammatically in Figures provided herein:
i. Mobile phase A: 5% MeOH in water
ii. Mobile phase B: 100% MeOH (Both water and MeOH are HPLC grade.)
iii. UV detection: 254 nm
iv. Gradient:
  1. Held at 5% B for 2 minutes
  2. Increased to 50% B in 13 minutes
  3. Increased to 95% B in 3 minutes
  4. Held at 95% B for 2 minutes
  5. Back to 5% B in 2 minutes
  6. Held at 5% B for 3 minutes.

Figure 3A:
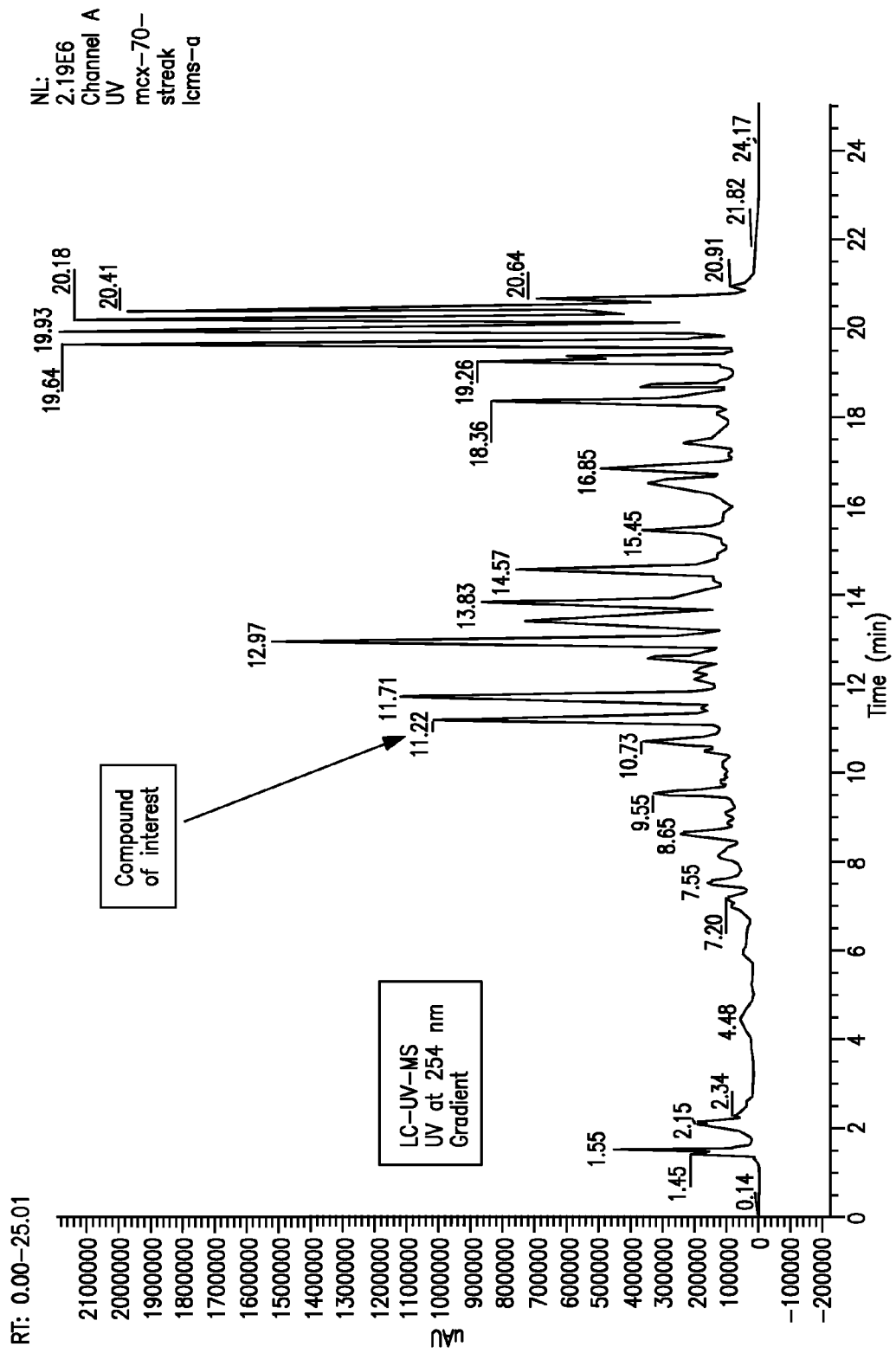
FIGS. 3A-B depict an exemplary chromatogram from first (gradient) HPLC separation.
Figure 3B:
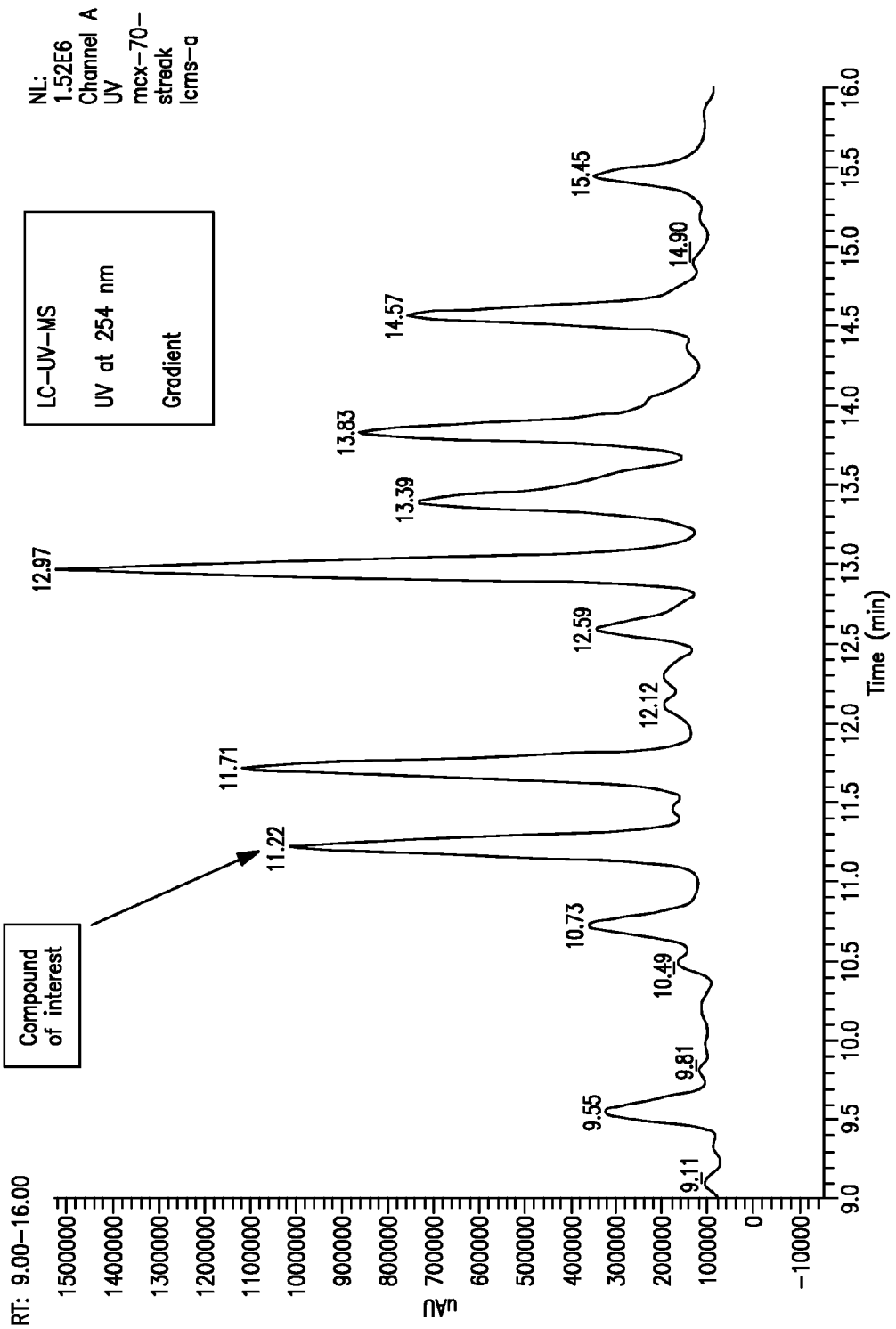
Figure 3C:
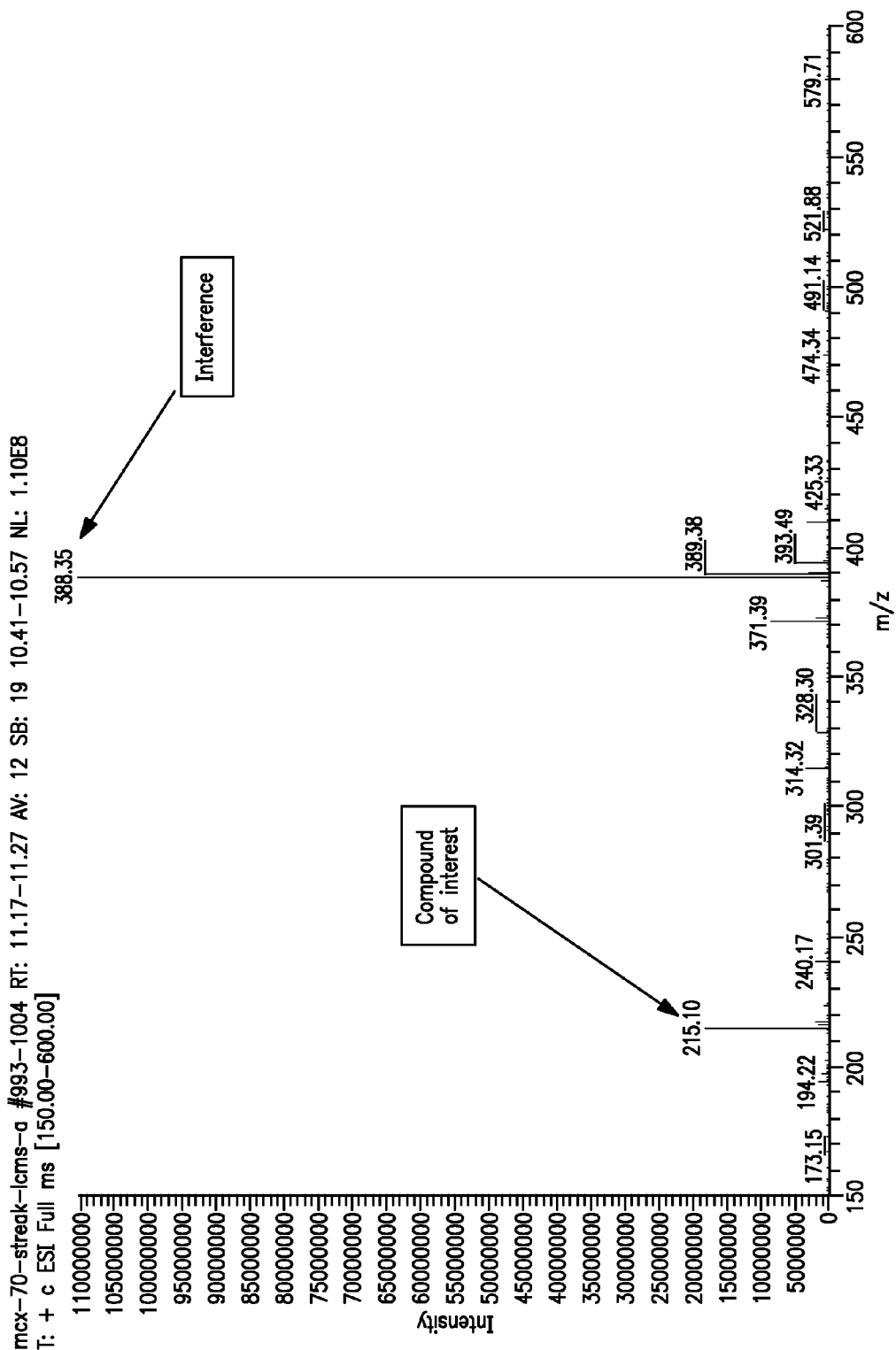
FIG. 3C depicts an exemplary mass spectrum of the fraction eluting at 11.2 minutes during the first chromatographic separation of the crude extract from mutant strain clavu7.

Under these conditions, the bioactive compound plus an additional hydrogen ([M+H]$^+$) eluted at around 11.3 minutes (FIGS. 3A-3C). It had a nominal mass to charge ratio (m/z) of 215 and co-eluted with another compound that had m/z=388. This ~11.3 minute fraction containing both compounds was collected and subjected to a second HPLC separation.

The conditions for the second HPLC run were:
i. Mobile phase A: 5% MeOH in water (same)
ii. Mobile phase B: 100% MeOH (same)
iii. UV detection: 254 nm (same)
iv. Isocratic 30% MeOH.

Under these conditions, one compound eluted at ~4.1 minutes ([M+H]$^+$ m/z=215 determined by high resolution MS) while the other compound ([M+H]$^+$ m/z=388) eluted at 3.2 minutes thus, allowing the two to be separated. The m/z=388 that eluted at 3.2 minutes compound was determined not to be bioactive in contrast to the m/z=215 compound that eluted at 4.1 minutes. The molecular formula of the bioactive compound with [M+H]$^+$ m/z=215 was determined to be $C_7H_7N_2O_2S_2$.

Example 2

Generation of Novel Compounds Using Mutagenesis

This example illustrates possible variations of the present method of competitive adaptive evolution.

The present method is not limited to competition/co-culture between only one producer versus only one competitor. The method can be carried out using more than two organisms. An exemplary system is one in which a producer microbe requires the presence of another microbe for growth. Both of these microbes would therefore be competed against the target organism. A need for another microbe might arise if it synthesizes an essential metabolite that the producer needs.

Both the producer and competitor can be genetically-modified variants of wild-type strains. For example, a drug resistance gene might be inserted into a strain that is normally sensitive to that particular drug. This modified organism could then be used as the competitor. As another example, an antibiotic biosynthetic gene cluster might be inserted or deleted from a producer. It would then be possible to use this mutant in an adaptive evolution/competition experiment against the target organism.

Mutagenesis can be used in numerous ways by employing this method. For example, the producer can be mutagenized prior to beginning the adaptive evolution-competition/co-culture.

It is expected that one of ordinary skill in the art executing this methodology would carry out multiple adaptive evolutions in parallel. In other words, multiple replicates of the same producer versus the target organism would be competed in an adaptive evolution environment rather than just one replicate of the producer.

Example 3

Purification of Holomycin

Figure 2:
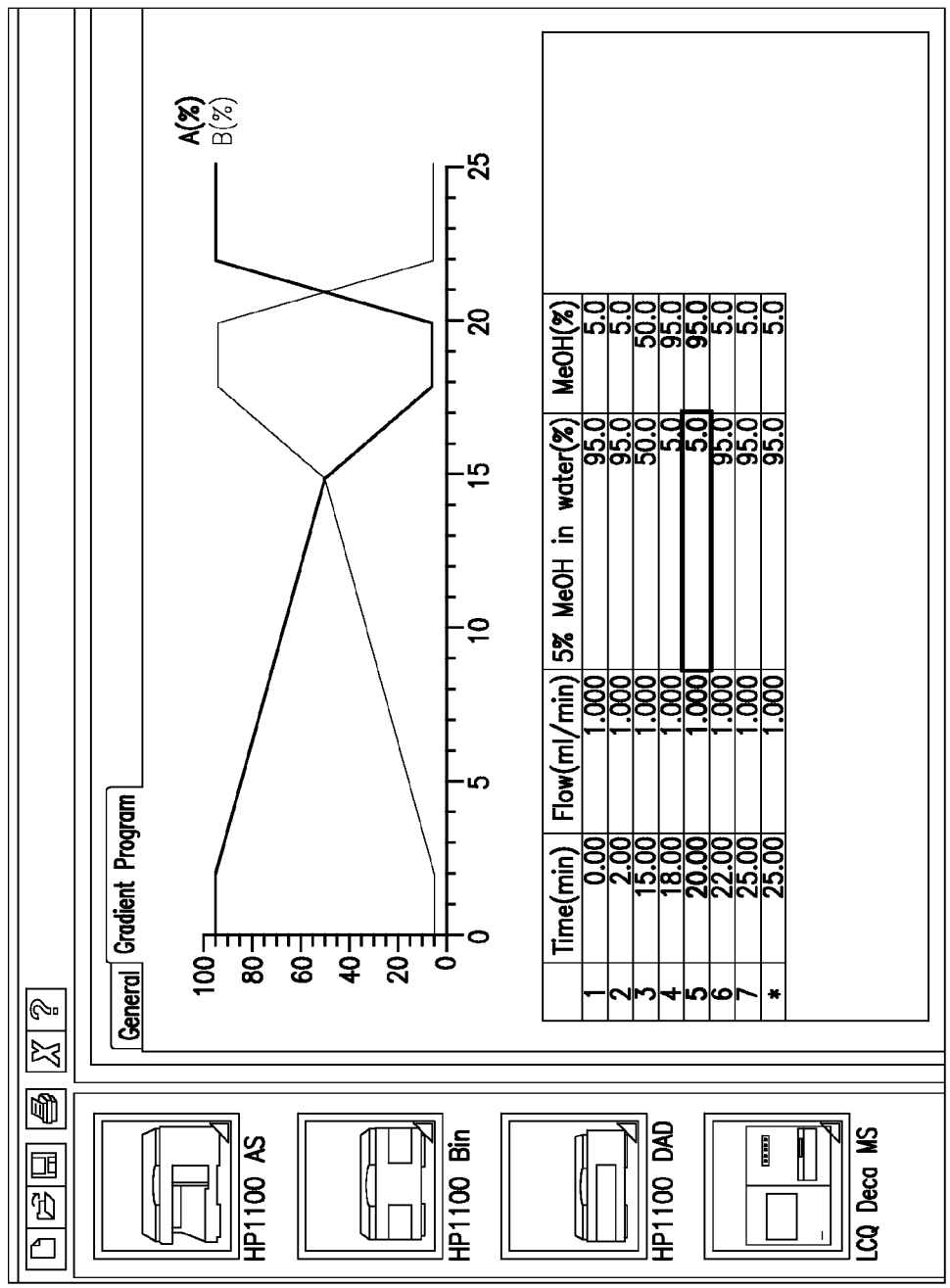
FIG. 2 is a diagrammatic representation of HPLC conditions used for a first chromatographic separation during isolation of bioactive compounds from a crude mixture.

The following example illustrates a procedure for the purification of holomycin.
a. Grow up a pre-culture of clavu7 from the frozen stock using TSB as the growth medium.
b. Once the preculture has grown up, adjust its optical density at 600 nm (OD600) such that it is between 0.08 and 0.13.

c. Make streaks of the OD600-adjusted clavu7 culture onto tryptic soy agar (TSA) plates.
d. Four days after the streaks are made, slice the agar with clavu7 on it into small pieces. This is most easily accomplished with a putty knife, mini food processor, or similar device.
e. Extract the clavu7/agar mixture with 100% methanol (MeOH) for 20-30 minutes. Use a volume of MeOH that is at least 3 times the volume of agar. A stir bar spinning at 150-200 rpm was used to mix the sample during extraction.
f. Remove the solid material and discard, e.g., by using a 0.22 micron membrane filter. Retain only the filtered MeOH for subsequent steps.
g. Evaporate the MeOH under vacuum until less than 5 mL remain, then dilute 1:39 with deionized water (DI water).
h. Perform solid phase extraction: pass the diluted solution through an Oasis MCX cation exchange column (Waters Corp, Waltham, Mass.) using the following protocol:
　i. Prep: 4 mL MeOH
　ii. Prep: 4 mL DI H2O
　iii. Load sample
　iv. Wash: 3 mL 2% HCOOH in water
　v. Wash: 3 mL DI H2O
　vi. Wash: 3 mL 20% MeOH in water
　vii. Elute and collect: 3 mL 70% MeOH in water
i. Concentrate the 70% MeOH fraction, e.g., by evaporating in a speed-vac.
j. Purification of holomycin requires two sequential HPLC separations of the concentrated 70% MeOH fraction. For both, the HPLC column was an Agilent C-18 column (Eclipse XDB-C18, 5 μm, 4.6 mm×150 mm) with flow rate of 1.0 ml/min. About 0.20 ml/min is delivered to the electrospray ionization (ESI) mass spectrometer and 0.80 ml/min is delivered to waste.
k. The HPLC conditions for the first run are as follows. These conditions are depicted diagrammatically in FIG. 2.
　i. Mobile phase A: 5% MeOH in water
　ii. Mobile phase B: 100% MeOH
　(Both water and MeOH are HPLC grade.)
　iii. UV detection: 254 nm
　iv. Gradient:
　　1. Held at 5% B for 2 minutes
　　2. Increased to 50% B in 13 minutes
　　3. Increased to 95% B in 3 minutes
　　4. Held at 95% B for 2 minutes
　　5. Back to 5% B in 2 minutes
　　6. Held at 5% B for 3 minutes.
l. Under these conditions, holomycin ([M+H]$^+$ m/z=215) elutes at around 11 minutes (FIG. 2A-2C). It co-elutes with another compound that has m/z=388. This ~11 minute fraction containing both compounds is collected and subjected to a second HPLC separation.
m. The conditions for the second HPLC run are:
　i. Mobile phase A: 5% MeOH in water (same)
　ii. Mobile phase B: 100% MeOH (same)
　iii. UV detection: 254 nm (same)
　iv. Isocratic 30% MeOH
n. Under these conditions, holomycin ([M+H]+ m/z 215) eluted at ~4.1 minutes.

Example 4

Structure Determination of Holomycin

Figure 4A:
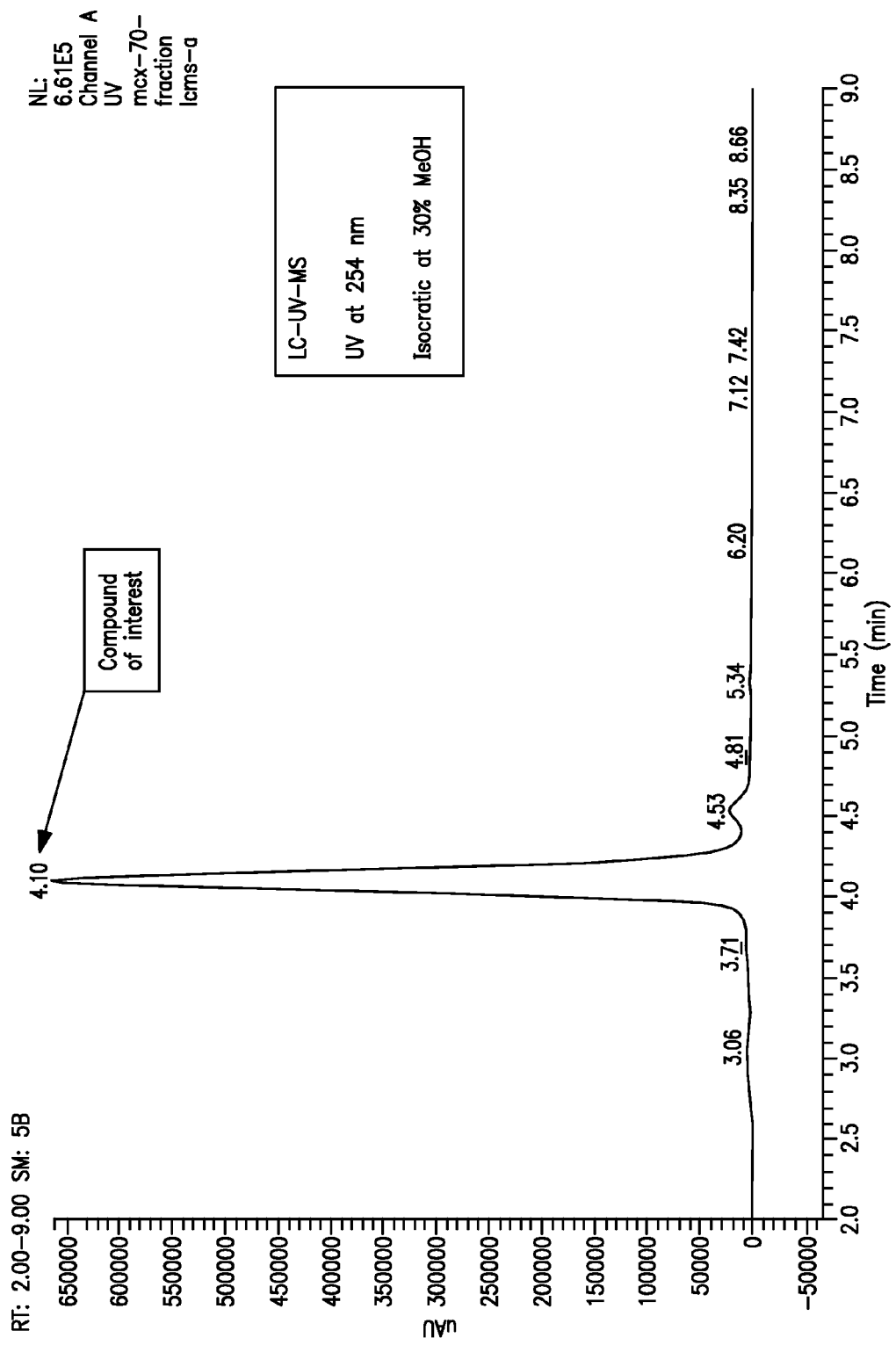
FIG. 4A is an exemplary chromatogram of a second (isocratic) HPLC run for the separation of two compounds that co-eluted at 11.2 minutes under the first chromatographic conditions.
Figure 4B:
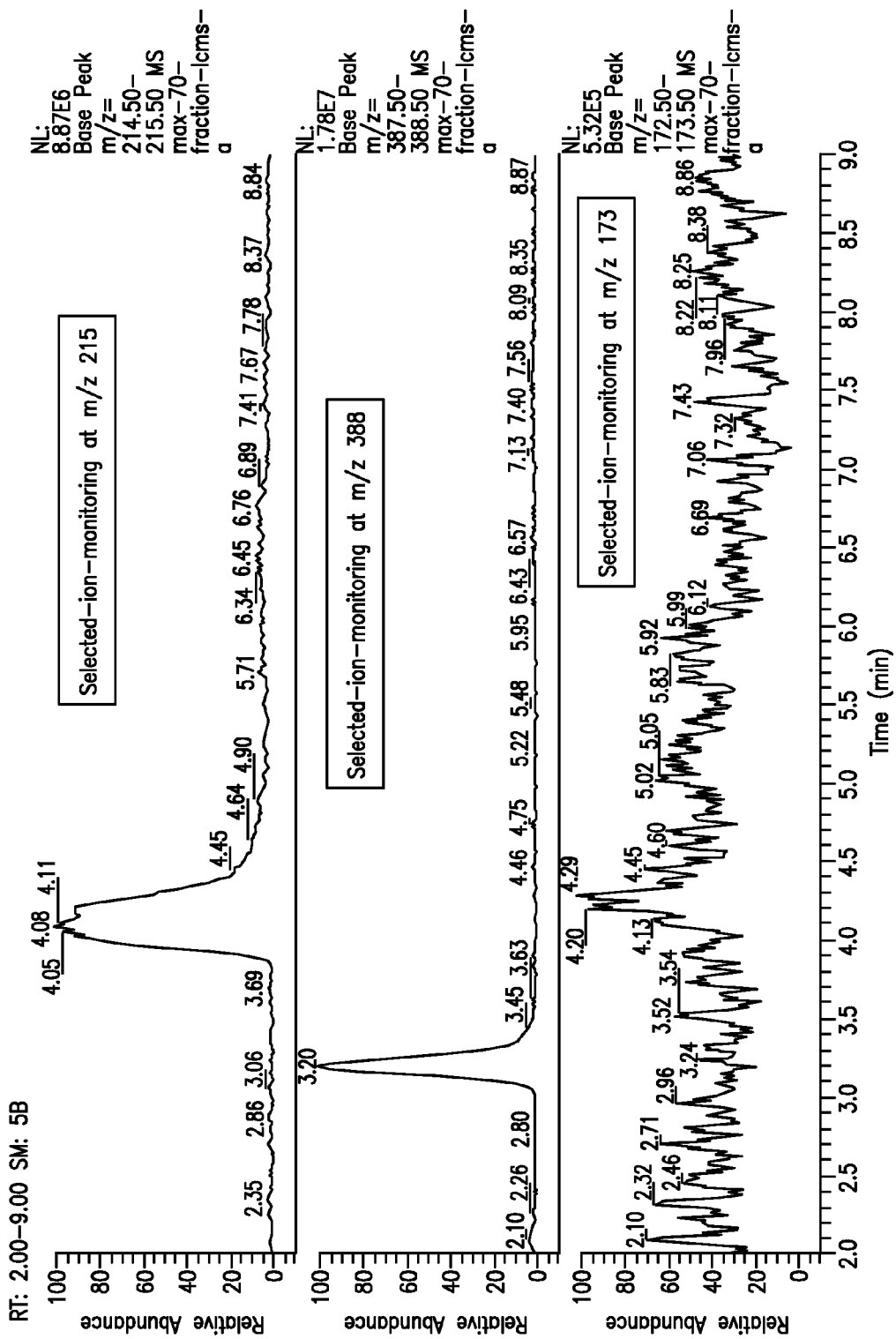
FIG. 4B shows select ion monitoring for mass-to-charge ratio (m/z)=215, 388 and 173 during second (isocratic) run. The compound of interest (m/z=215) has a longer retention time than the m/z=388 compound, allowing the two to be separated. The m/z=173 peak is a fragment of the m/z=215 peak.
Figure 4C:
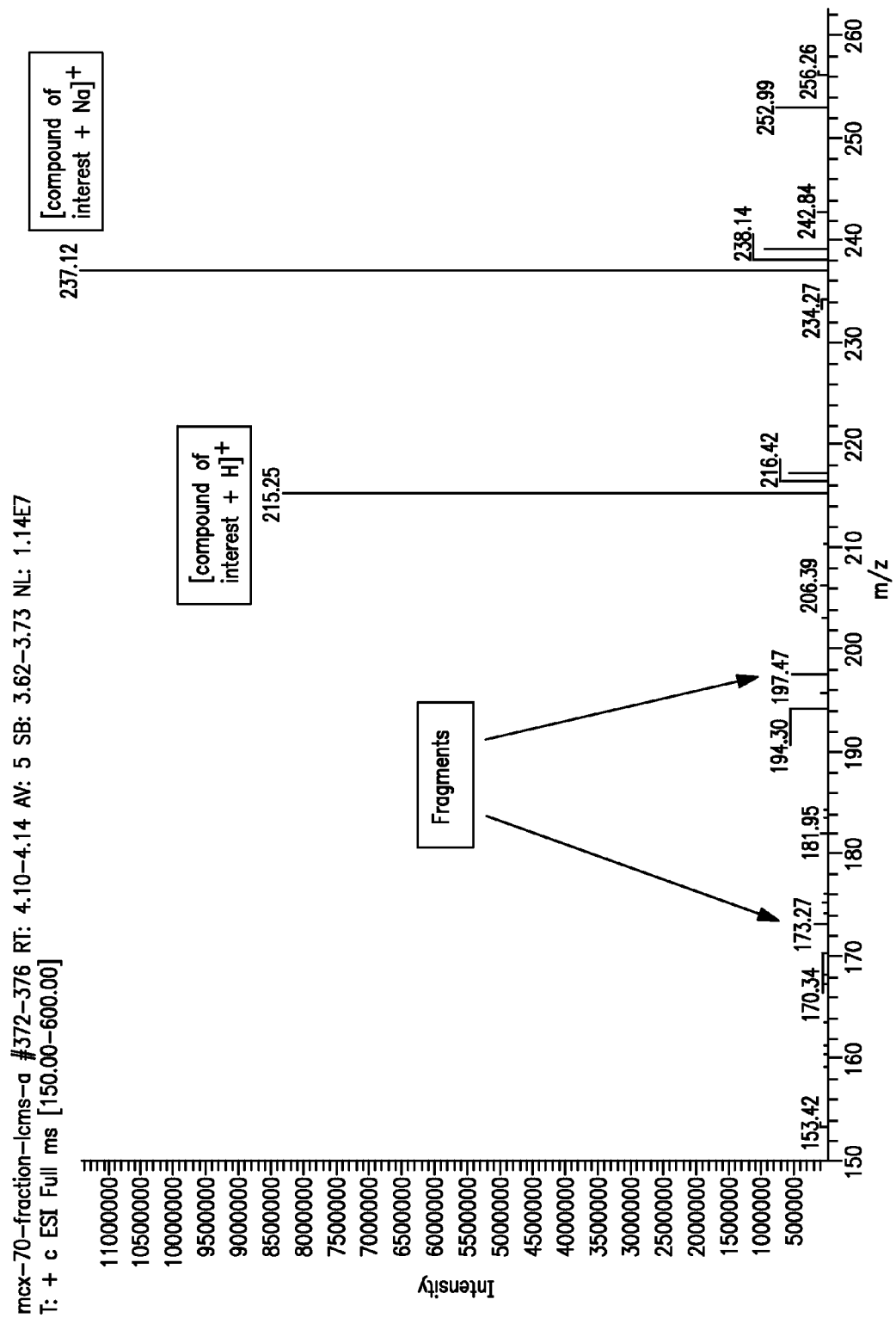
FIG. 4C shows an exemplary mass spectrum of fraction collected at 4.1 minutes during the second (isocratic) chromatographic separation of co-eluting compounds under the first set of HPLC conditions.
Figure 4D:
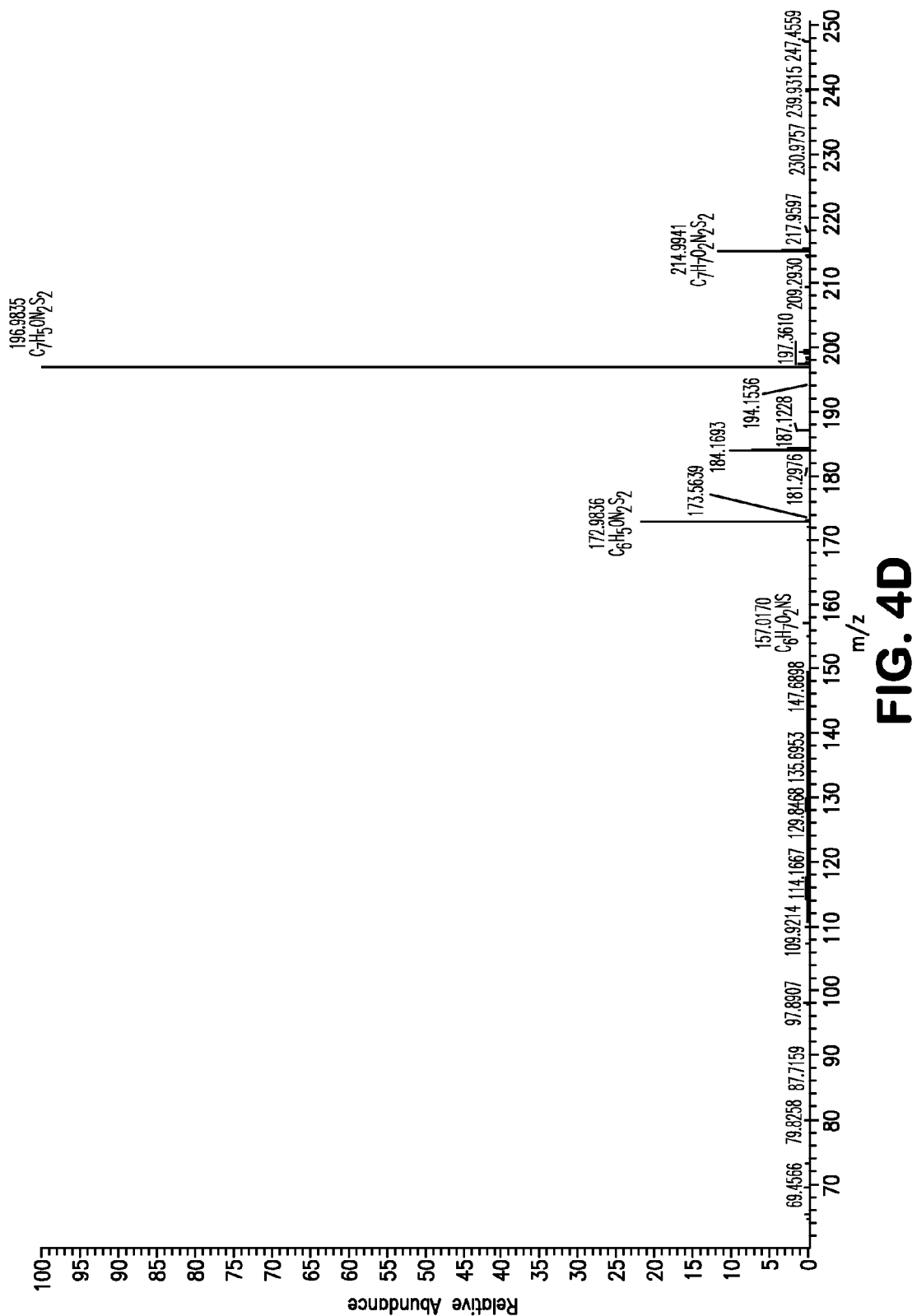
FIG. 4D shows MS/MS analysis of m/z=215 using high resolution ESI-FT-MS (Orbit-Trap-MS). There are distinct peaks at m/z=214.9941, 196.9835, 184.1693 and 172.9836.
Figure 5:
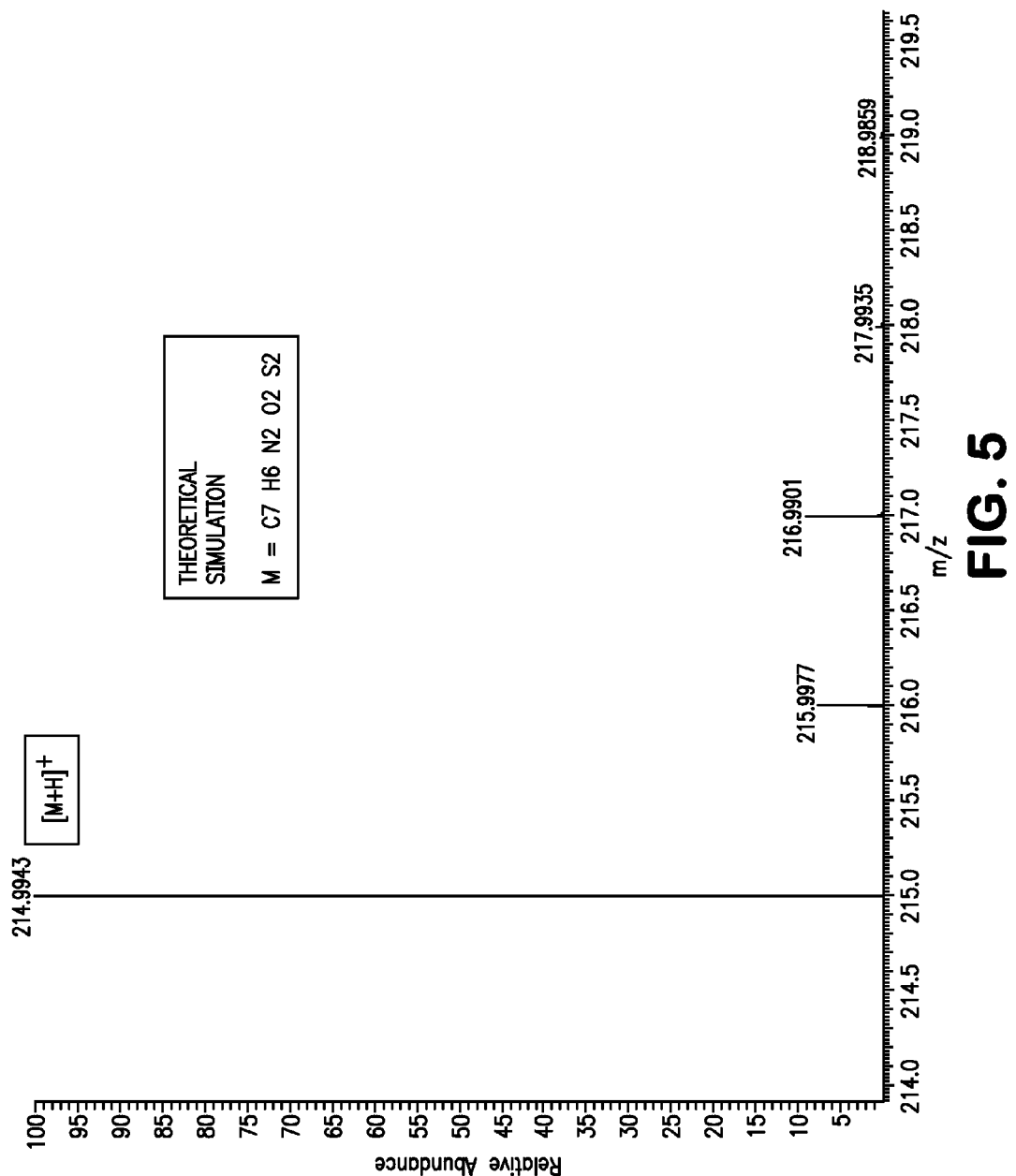
FIG. 5 shows a theoretical mass spectrum of $C_7H_7N_2O_2S_2$. This confirms the molecular composition of the 214.9941 peak in FIG. 6A.
Figure 6A:
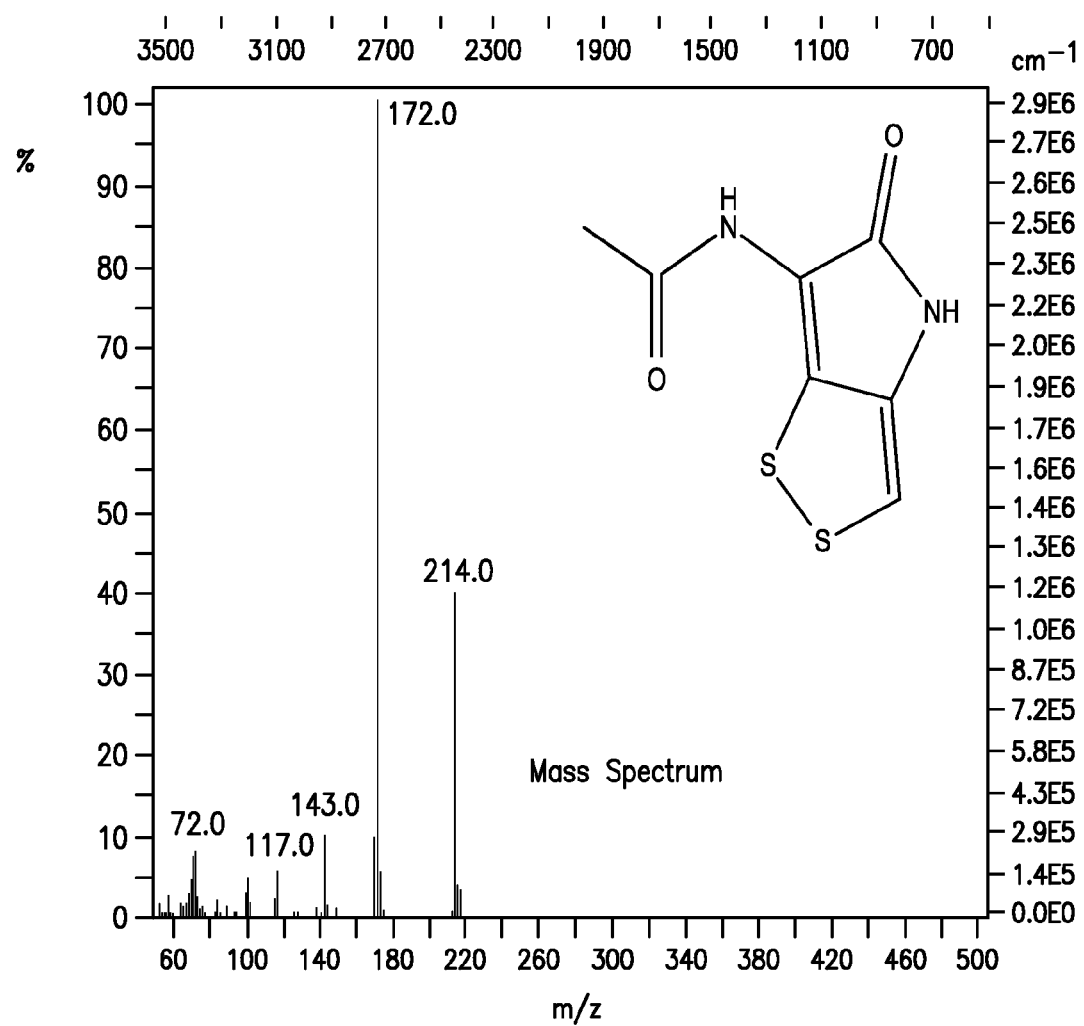
FIG. 6A is an exemplary mass spectrum of pure holomycin.
Figure 6B:
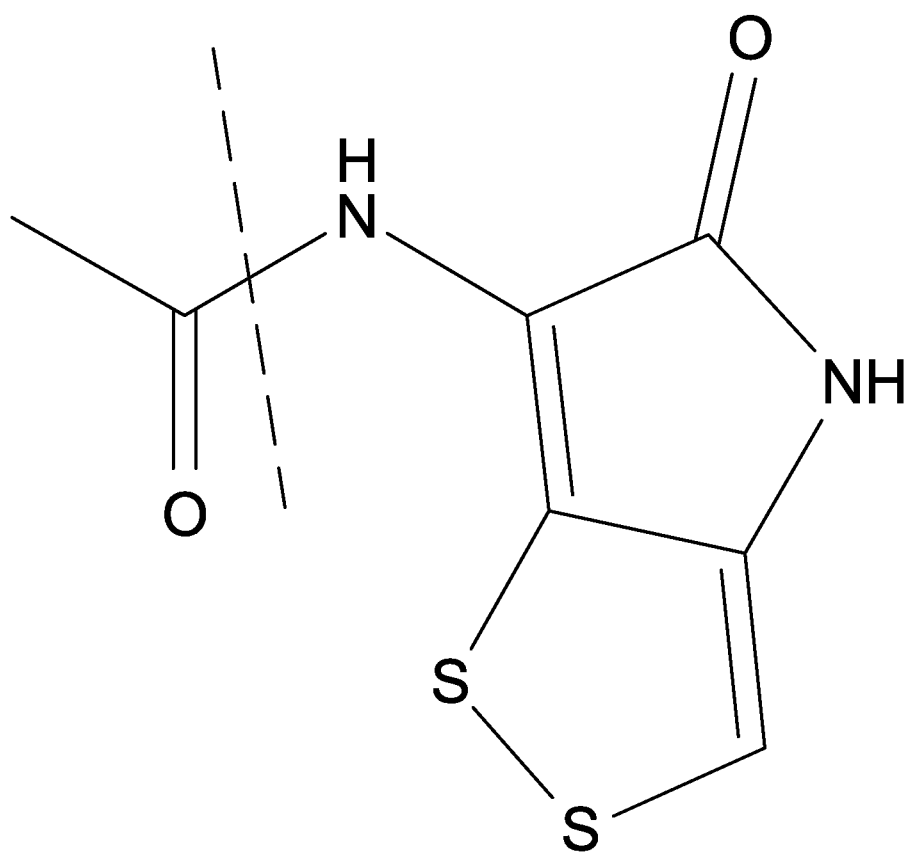
FIG. 6B shows the chemical moiety (right hand side of dashed line) that gives rise to the m/z 172 fragment peak in the holomycin mass spectrum (FIG. 6A).

This example illustrates that the structure of holomycin isolated from clavu7 strain was elucidated chiefly through analysis of the high-resolution MS/MS data (FIGS. 4D and 5).

The molecular formula with proton ([M+H]$^+$) was determined to be $C_7H_7N_2O_2S_2$ based on a high-resolution molecular mass of 214.9941 (FIG. 5). Therefore, the molecular formula for the actual compound is $C_7H_6O_2N_2S_2$ with a molecular weight of 213.99.

There are additional prominent peaks in the MS/MS at m/z=196.9835 and 172.9836 (FIG. 4D). Like the 214.9941 m/z peak, both have a proton attached. In other words, the true molecular weights for these fragments are 196 and 172 when rounded to the nearest integer.

Holomycin, a known antibacterial produced by wild-type *S. clavuligerus*, has a molecular weight of 213.99. When a sample of pure holomycin was analyzed by HPLC-MS, it produced a mass spectrum that was identical to that of the compound isolated from clavu7 that eluted at 4.1 minutes (as described above). Therefore, the bioactive compound produced by clavu7, was identified as holomycin (FIG. 9).

Example 5

Induction and Identification of Genomic Mutations

This example illustrates that more than one genomic mutation can be induced and identified by the present method of competitive adaptive evolution. This example further illustrates that genomic mutations in a producer may be used to up-regulate the biosynthesis of bioactive compounds.

During the adaptive evolution process, mutations frequently arise in the producer organism that lead to increased biosynthesis of bioactive compounds. For example, a certain bioactive compound might be synthesized at a low level in the strain of the producer that is used to start the adaptive evolutionary process, but mutations can arise during adaptive evolution that sharply increase the amount of the compound that is produced. The location of these mutations within the genome and the precise identity of the mutations e.g., SNPs or indels, are important. In the event it is desirable to engineer a *Streptomyces* strain at a later time to produce greater amounts of the compound than what can be obtained from the wild-type strain, then these mutations would be natural starting points for genome modification.

The induction and identification of genomic mutations in a producer may be used to up-regulate the biosynthesis of bioactive compounds as follows:

Apply the adaptive evolutionary process as described above by co-culturing two or more organisms where at least a first organism is a producer and at least a second organism is a target.

Perform whole-genome re-sequencing of an evolved producer strain (for example, clavu7 or NL2-c4) or partial re-sequencing of selected genomic regions.

Introduce mutations back into the parental, wild-type strain singly or in combination. This would be achieved by one of two means: The first is inactivating the wild-type copy of the gene of interest from the wild-type strain and then introducing the mutant copy found after adaptive evolution into the wild-type strain. The mutant gene can be integrated into the chromosome of the organism, or it can be borne on an extra-chromosomal DNA element such as a plasmid, cosmid, fosmid, or bacterial artificial chromosome. The second is inactivating the mutant copy of the gene of interest in the evolved strain isolated after adaptive evolution and then introducing the wild-type copy into the evolved strain. Again, the wild-type copy can be introduced into the evolved strain by either integrating the wild-type copy into the chromosome of the organism or on an extra-chromosomal DNA element.

Analyze the strain with the mutant gene copy or copies for production of the bioactive compound of interest. The analytical procedure would be essentially identical to that used to find the bioactive compound from the evolved strain using HPLC-MS. This analysis would determine which mutations actually impact production of the compound of interest versus mutations that have no effect.

When clavu7 was sequenced, 6 mutations were found that were not present in the starting, wild-type strain. The five mutations are listed in Table 1 below.

The following process, which was used to find mutations in clavu7, could be employed to find mutations in any other strain.

DNA was extracted from clavu7. The DNA was subsequently sequenced using a commercially available high-throughput sequencing technology from Illumina. Other companies such as Life Technologies also offer similar technology. The resulting sequencing data was mapped back onto the reference (wild-type) genome to identify possible differences (mutations) between the genome of clavu7 and wild-type S. clavuligerus. There are many algorithms that perform this task that are freely available in the public domain.

The putative mutations were verified through use of traditional Sanger sequencing: primers were designed to PCR-amplify each region of DNA that contained the putative mutation and then sequenced. Sanger sequencing is a common technology that is widely used in the biotechnology field.

TABLE 1

List of Mutations Detected in Clavu7.

| | Broad locus ID[1] | DSM locus ID | Annotation | SNP |
|---|---|---|---|---|
| 1 | SSCG_02612 | SCLAV_2674 | WD-40 repeat-containing protein | C1096T |
| 2 | SSCG_05972 | SCLAV_3742 | malate dehydrogenase | C570A |
| 3 | SSCG_00146 | SCLAV_4200 | N-(5-amino-5-carboxypentanoyl)-L-cysteinyl-D-valine synthase | G4573C |
| 4 | SSCG_05988 | SCLAV_5196 | glycosyl hydrolase | G1245A |
| 5 | SSCG_06722 | SCLAV_5104 | pyrroloquinoline quinone biosynthesis protein B | G433A |
| 6 | — | — | Deletion of the pSCL4 plasmid | |

[1]The Broad locus IDs are taken from accession number ABJH00000000. The DSM locus IDs are taken from accession number ADGD00000000. The SNP positions are based on Broad locus IDs.

Example 7

Generation and Identification of NL2-c4 Strain

This example illustrates that numerous discrete strains, which produce different bioactive compounds, can be generated in tandem by performing multiple adaptive evolutions in parallel.

Generation of the NL2-c4 strain was done in parallel with the clavu7 strain according to the method described above. While the identity and chemical structures of the bioactive compounds from NL2-c4 have not yet been elucidated, it has been established that the bioactive compounds produced by this strain do not include holomycin.

The adaptive evolutionary process described in Example 1 was initiated with multiple replicates of S. clavuligerus and the replicates evolved in parallel. One of the replicates resulted in clavu7, and another replicate resulted in numerous different mutant strains, including one called NL2-c4.

According to the method described above, NL2-c4 has been determined to produce more than one bioactive compound. Holomycin is not one of these bioactive compounds. Therefore, the adaptive evolutionary process has resulted in at least two discrete strains that produce two different sets of bioactive compounds. It is expected that analysis of additional strains will lead to discovery of additional distinct sets of bioactive compounds.

The analysis protocol for bioactive antibacterial compounds from NL2-c4 is as follows:

A culture of NL2-c4 was prepared by inoculating mycelia or spores into trypticase soy broth (TSB). The mycelia/spores are frequently stored long-term at −80° C., but they may also come from other sources such as a colonies on an agar plate.

The culture was incubated at 28-30° C. and aerated by spinning the culture broth using a magnetic stir bar placed inside the flask or by shaking the entire flask.

The optical density of the culture was monitored and once the culture had an optical density at 600 nm (OD600) between 0.08 and 0.13, 2 μL were deposited onto each of nine spots spaced equidistantly on a standard 100×15 mm petri dish containing trypticase soy agar. The size of the petri dish and the number of spots made from the culture can both vary. If the density of the culture exceeded 0.13, the culture was diluted with TSB until its OD600 value fell between 0.08 and 0.13.

The TSA plates were incubated for 4 days at 28° C. On the fourth day, agar plugs containing the NL2-c4 colonies and extending approximately 4-6 mm beyond the edge of colony were excised from the rest of the agar plate and cut into small pieces. NL2-c4 colonies were removed from the agar plate prior to this step by scraping them off the plates.

The diced agar pieces were soaked in a mixture of 1:2 methanol:methylene chloride for 20-30 minutes with gentle agitation or stirring. The supernatant was carefully decanted or filtered to separate the agar from the solvent mixture. The process of soaking the agar pieces and filtering or decanting the methanol:methylene chloride extract was repeated two to three times and the extracts were combined into one sample, which was concentrated using a rotary evaporator with a bath temperature set at 35° C.

The ensuing concentrated sample was diluted 1:39 with water, then passed through a solid phase extraction (SPE) column. The specific SPE column used here was an Oasis HLB column sold by Waters Corp. (Waltham, Mass.). The protocol and chromatography conditions are as follows:
  Prep: 4 mL MeOH
  a. Prep: 4 mL deionized water
  b. Load sample. Maintain flow rate at 4-6 mL/minute
  c. Wash: 4 mL 5% MeOH in water
  d. Elute and collect: 1.5 mL 100% MeOH The methanol sample was then concentrated further using a vacuum centrifuge (speed-vac or speed-yap) until approximately 100 μL remained. A 25 μL aliquot was then used to test for bioactivity against MRSA N315. This aliquot, which has not yet been fractionated on an HPLC system, is called a "crude extract." About 40-50 μL of the concentrated sample was also injected into an HPLC-MS system. The HPLC, MS, and C18 column (Agilent 4.6 mm×150 mm C18 column) used during this analysis were identical to those used to analyze bioactive extracts from clavu7. The mobile phase was:
Solvent A: 2.5% methanol in water
Solvent B: 100% methanol
  a. Hold at 50% B for 5 minutes.

b. Linear increase from 50% B to 95% B over 20 minutes
c. Hold at 90% B for 10 minutes.

Figure 7A:
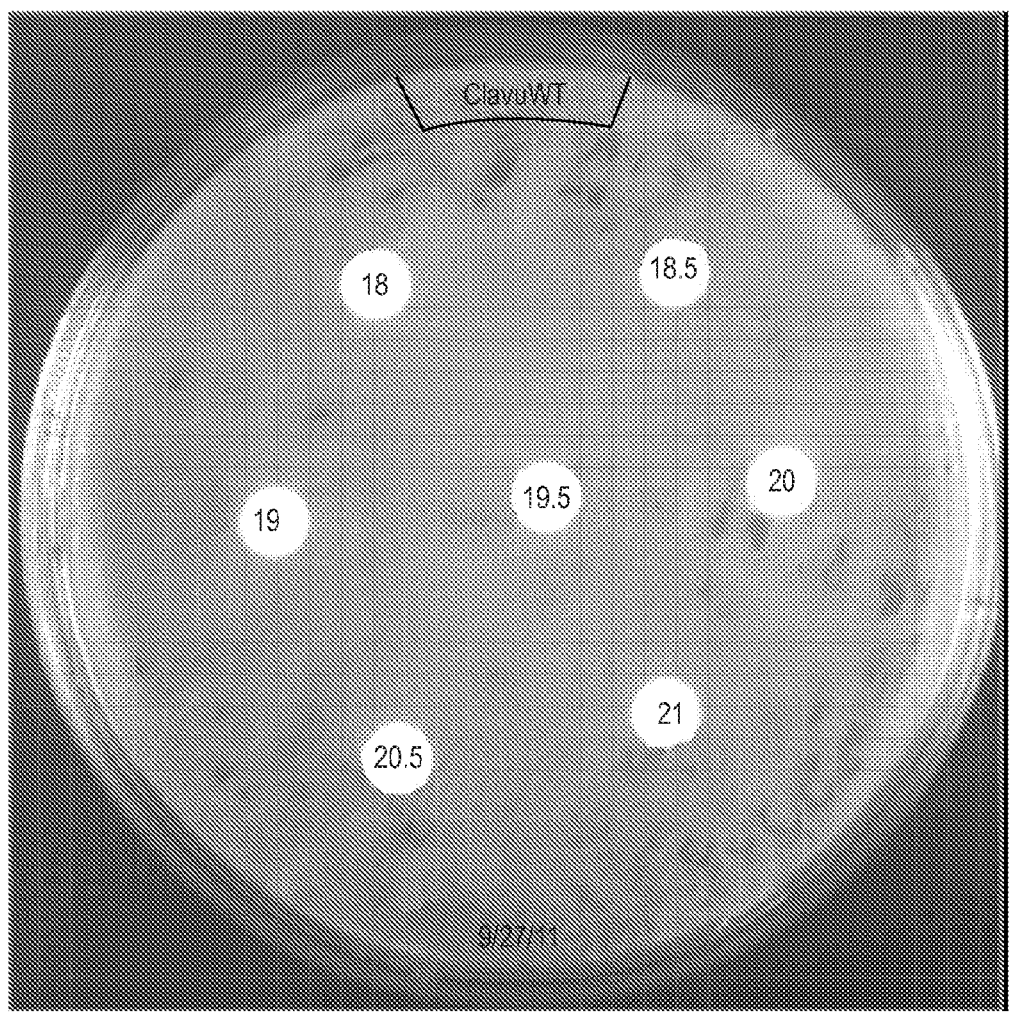
FIGS. 7A-D are photographs of cultures of MRSA N315 plated against wild-type (A-B) and a mutant (C-D) strain of *S. clavuligerus* referred to as NL2-c4. The extracts from both strains were fractionated and collected in half-intervals over a full 30 minute HPLC run and then assayed for bioactivity. Inhibition of growth was indicative of a bioactive fraction as shown in FIG. 7C-D for the mutant strain.
Figure 7B:
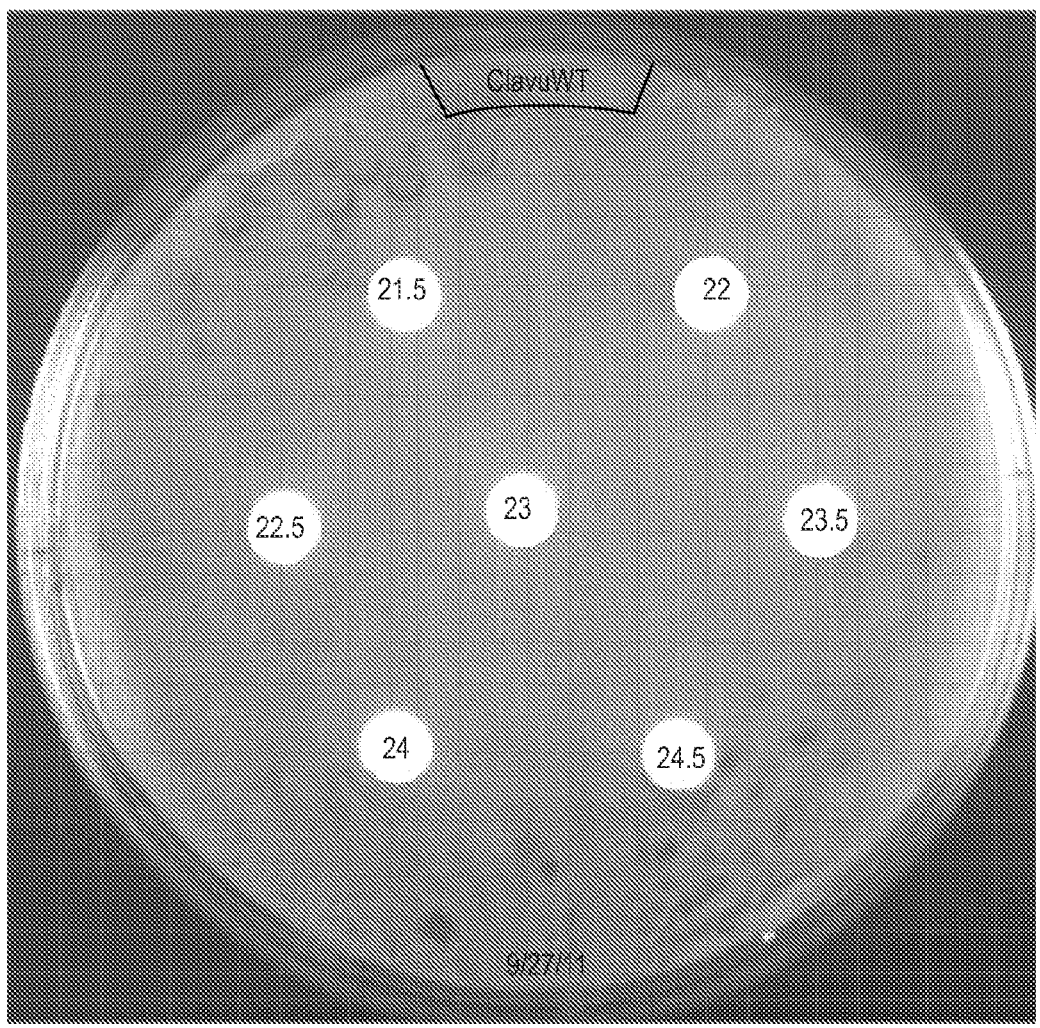
Figure 7C:
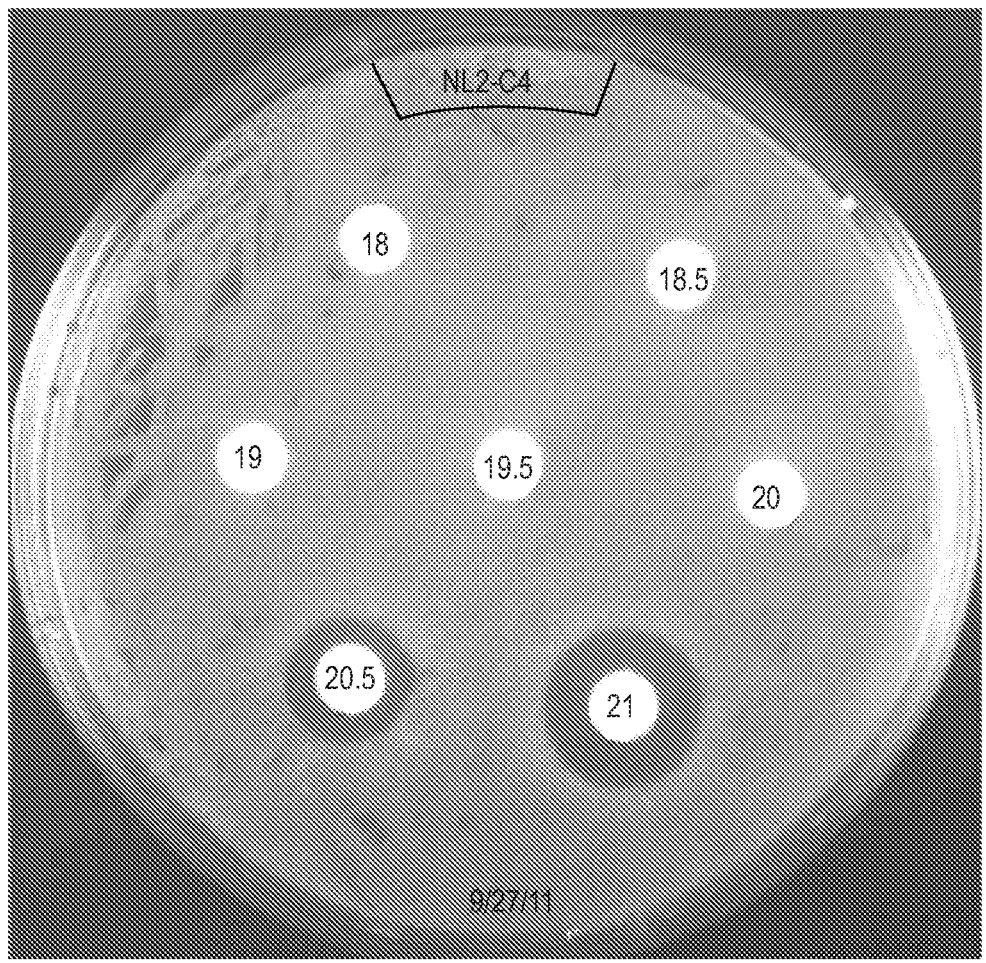
Figure 7D:
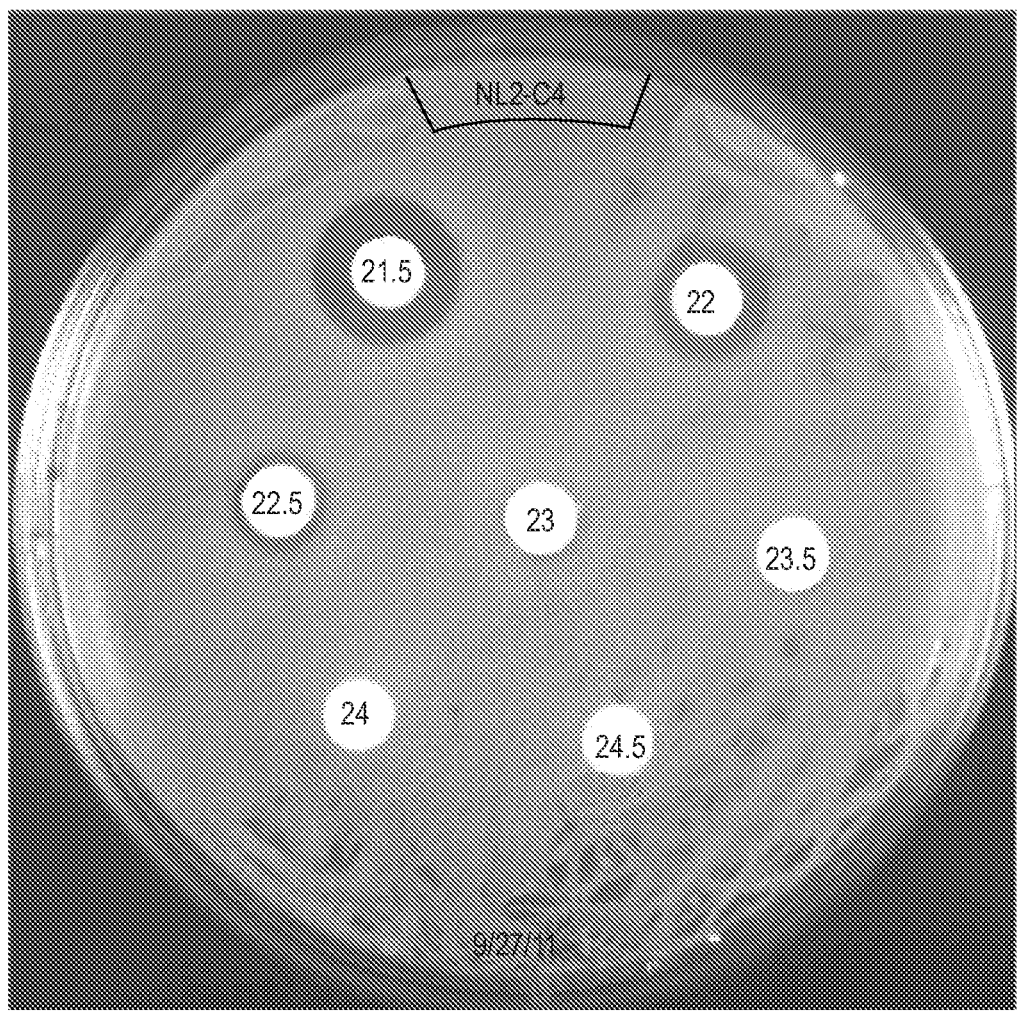

Fractions were collected in half-minute intervals over the full 35 minute run. Each of the fractions was then concentrated to 50 µL using a speed-yap, after which 25 µL was tested for bioactivity against MRSA N315 using a standard agar diffusion assay. The following time points showed bioactivity as defined by the presence of a zone of inhibition (ZOI) surrounding a paper disk approximately 24 hours after the disk was impregnated with one of the fractions collected from the HPLC. The crude extract for NL2-c4 also showed strong bioactivity (see FIG. 7B).

a. 20.5-21 minutes
b. 21-21.5 minutes
c. 21.5-22 minutes
d. 22-22.5 minutes
e. 22.5-23 minutes
f. crude extract Using the exact same protocol described above, the extracts of the starting, wild-type strain of *S. clavuligerus* used to initiate the adaptive evolutionary process against MRSA N315 were also analyzed, which served as a negative control. As shown in FIG. 7A, the wild-type samples did not show bioactivity between 20.5 and 23 minutes in contrast to the NL2-c4 fractions. This comparative analysis between NL2-c4 versus wild-type *S. clavuligerus* extracts demonstrates that the adaptive evolutionary process directly led to the mutant strain NL2-c4, which produces bioactive compounds against MRSA N315.

Figure 8A:
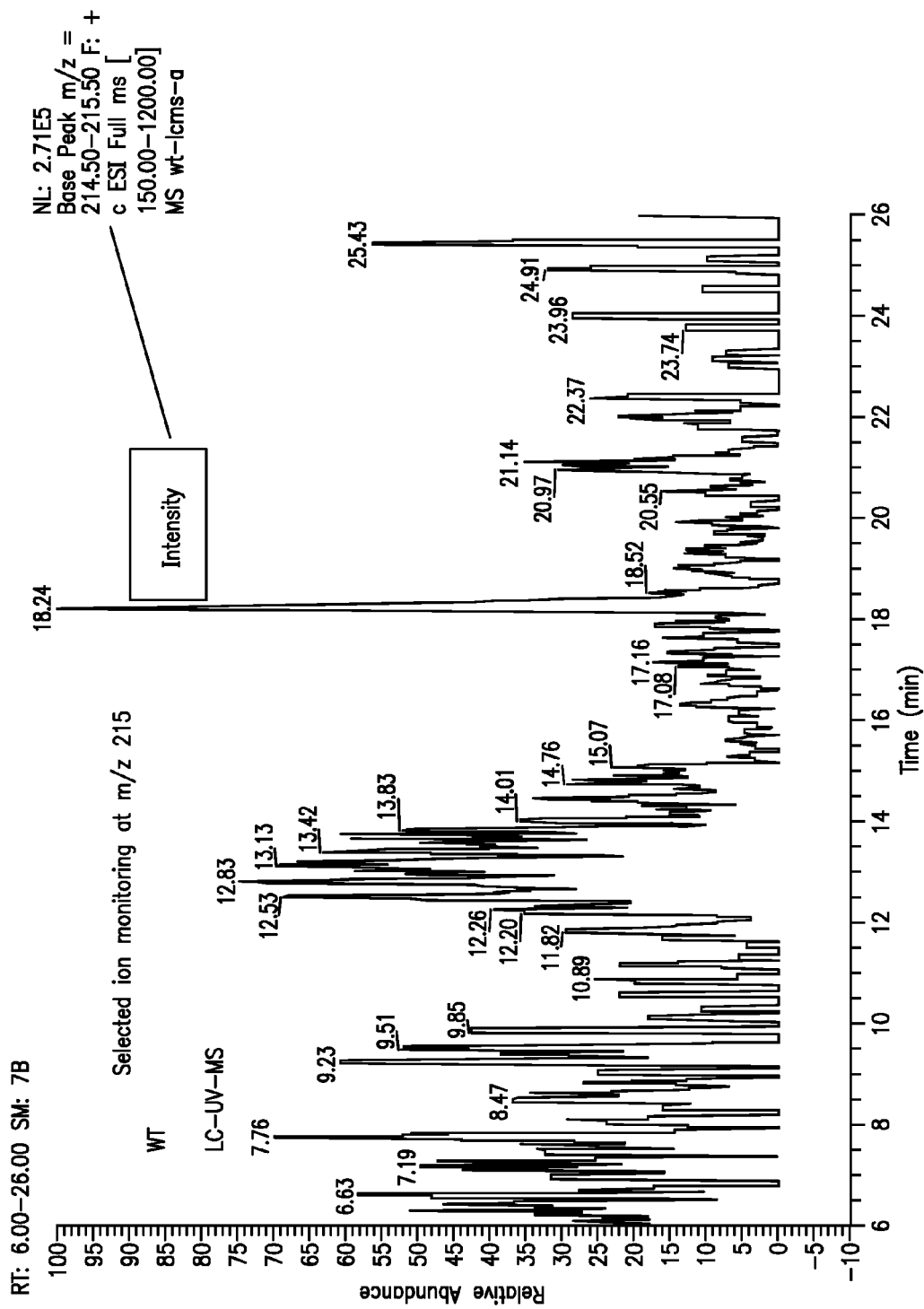
FIGS. 8A-B depict select ion monitoring (SIM) for wild-type and the NL2-c4 mutant strain of *S. clavuligerus*. A. SIM for m/z=215 from extracts of wild-type clavuligerus, which is the mass-to-charge ratio for holomycin as detected. B. SIM for m/z=215 from extracts of NL2-c4.
Figure 8B:
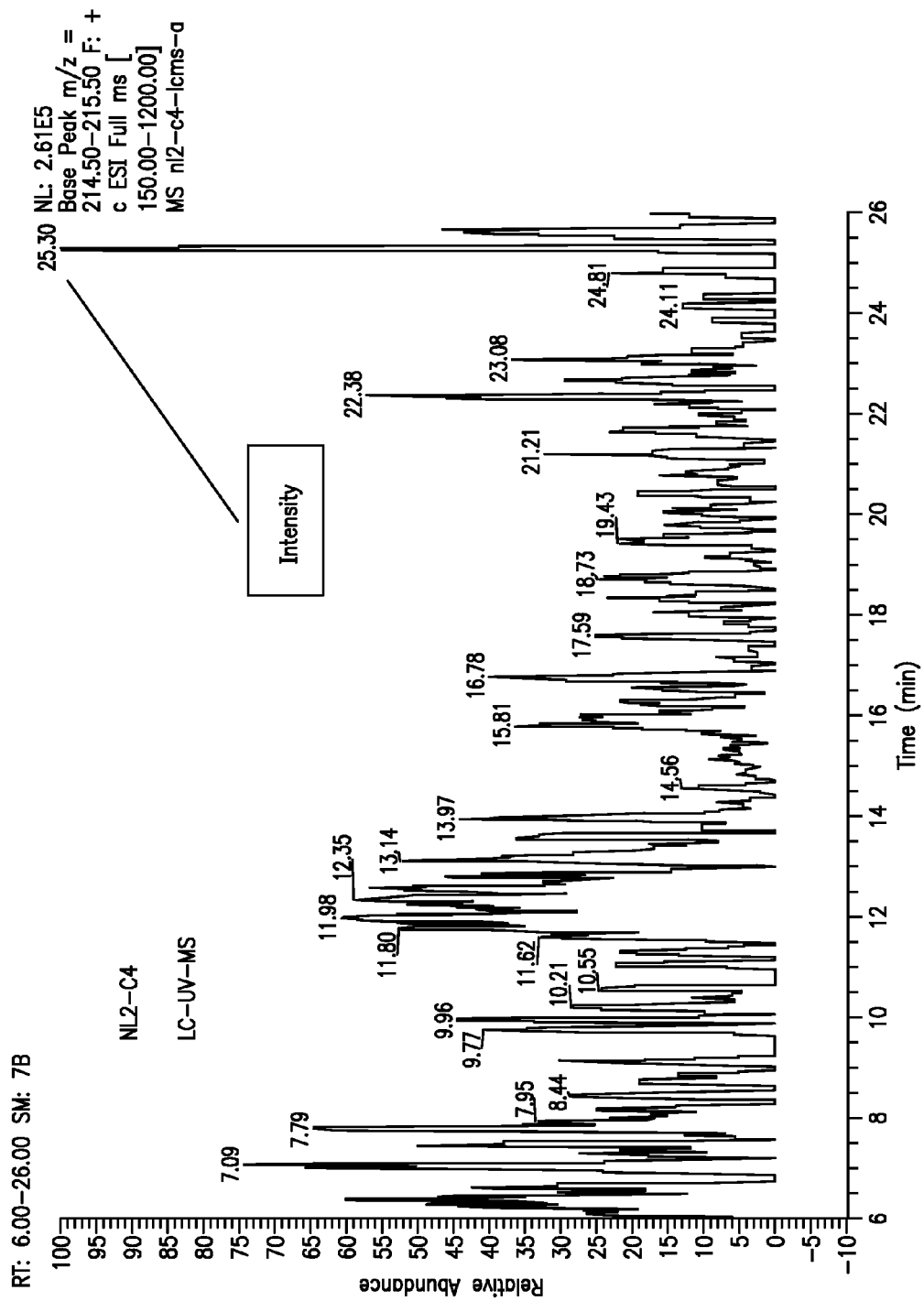

Based on data from clavu7, holomycin is known to have a mass to charge ratio (m/z) of 215 when it is present in a sample and detected in by HPLC-MS. Thus, the MS data from NL2-c4 was examined for the presence of an m/z 215 fragment in the bioactive range between 20.5 and 23 minutes, to investigate the possibility that one of the bioactive fractions from NL2-c4 contained holomycin. The MS data, however, indicated that no compound with m/z 215 was present in the NL2-c4 extracts between 20.5 and 23 minutes (see FIG. 8). FIG. 8 shows select ion monitoring (SIM) for m/z 215 from extracts of wild-type (top) and mutant (bottom) clavuligerus and indicates that a compound from wild-type with m/z 215 elutes at 18.24 minutes, but this sample was not bioactive. We therefore conclude that this compound at 18.24 minutes has a similar molecular formula to holomycin but is not holomycin itself. In contrast, no compound with this mass-to-charge ratio can be detected within the range of 20.5-23 minutes from NL2c-4, which is the time window in which bioactive compounds elute thereby indicating that holomycin is not one of the bioactive compounds produced by NL2-c4. Therefore, the bioactivity seen in the NL2-c4 extracts arose from a different set of compounds, a set that does not include holomycin.

The chemical structures of bioactive compounds produced by the NL2-c4 mutant strain and other mutant strains can be elucidated according to the methods described above and known in the art (e.g., MS, NMR, IR, UV-vis, elemental analysis).

Thus, the adaptive evolutionary process described herein led to at least two different mutant strains each producing two distinct sets of bioactive compounds. The same adaptive evolutions, performed on a greater number of replicates or used on a greater number of different producers of bioactive compounds such as other *Streptomyces* species, myxobacteria, or certain fungi, would lead to the discovery of additional mutant strain and even more bioactive compounds, some of which would include NCEs.

Although the invention has been described with reference to the above example, it will be understood that modifications and variations are encompassed within the spirit and scope of the invention. Accordingly, the invention is limited only by the following claims.

What is claimed is:

1. A method for identifying a bioactive compound in a culture comprising:
   (i) co-culturing two or more organisms, wherein at least one organism is a parent producer organism and at least one other organism is a target and wherein the parent producer organism is *Streptomyces clavuligerus* and produces holomycin;
   (ii) detecting inhibition of growth of the target organism(s);
   (iii) isolating from the co-culture the parent producer organism after the detecting of OD;
   (iv) repeating (i)-(iii) at least once with the isolated producer and the target to produce an evolved strain of the parent producer, wherein the evolved strain may or may not produce holomycin; and
   (v) detecting the presence of one or more bioactive compounds in the co-culture in addition to or other than holomycin, thereby identifying a bioactive compound produced by the evolved producer organism.

2. The method of claim 1, further comprising isolating from a producer at least one compound with bioactivity against the target(s) from the co-culture of (i).

3. The method of claim 1, further comprising identifying the bioactive compounds by chemical structure elucidation means.

4. The method of claim 3, wherein the chemical structure elucidation means is mass spectrometry (MS) or nuclear magnetic resonance spectroscopy (NMR).

5. The method of claim 1, wherein the co-culture comprises *Streptomyces clavuligerus*.

6. The method of claim 1, wherein the co-culture comprises *Staphylococcus aureus*.

7. The method of claim 1, wherein detection of inhibition of growth of the target organism is the appearance in the co-culture of a zone of inhibition (ZOI).

* * * * *